United States Patent [19]
Imamura et al.

[11] Patent Number: 6,004,772
[45] Date of Patent: *Dec. 21, 1999

[54] OXYGENASE EXPRESSING MICROORGANISM STRAIN JM1 (FERM BP-5352) FOR DEGRADING ORGANIC COMPOUNDS WITHOUT AN INDUCER

[75] Inventors: Takeshi Imamura, Chigasaki; Tetsuya Yano, Isehara; Masahiro Kawaguchi, Atsugi; Shinya Kozaki, Tokyo; Yuji Kawabata, Isehara, all of Japan

[73] Assignee: Canon Kabushiki Kaisha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/608,808

[22] Filed: Feb. 28, 1996

[30]   Foreign Application Priority Data

| Feb. 28, 1995 | [JP] | Japan | 7-040377 |
| Feb. 28, 1995 | [JP] | Japan | 7-040380 |
| Feb. 28, 1996 | [JP] | Japan | 8-041100 |

[51] Int. Cl.$^6$ .............................. B09B 3/00; C10G 32/00; C12N 1/12; G01N 33/53
[52] U.S. Cl. ................................. 435/34; 210/601; 435/4; 435/29; 435/252.1; 435/262.5; 435/262; 435/281; 435/308.1; 435/821; 435/822; 435/843; 435/975
[58] Field of Search ................................ 435/252.1, 262, 435/262.5, 281, 822, 4, 29, 34, 308.1, 821, 843, 975; 424/93.4, 94.1; 210/601

[56]   References Cited

U.S. PATENT DOCUMENTS

| 4,654,303 | 3/1987 | Hagedorn | 435/172.3 |
| 4,877,736 | 10/1989 | Fliermans | 435/183 |
| 4,925,802 | 5/1990 | Nelson et al. | 435/262 |
| 5,316,940 | 5/1994 | Georgrou et al. | 435/252.1 |
| 5,543,317 | 8/1996 | Shield et al. | 435/240.2 |

FOREIGN PATENT DOCUMENTS

| 2-92274 | 4/1990 | Japan | C12N 1/20 |
| 2-273599 | 11/1990 | Japan | C02F 3/34 |
| 3-292970 | 12/1991 | Japan | A62D 3/00 |
| 6-70753 | 3/1994 | Japan | C12N 1/20 |
| 6-105691 | 4/1994 | Japan | C12N 15/53 |
| 6-22769 | 6/1994 | Japan | C12P 1/04 |
| 6-261776 | 9/1994 | Japan | C12P 17/16 |
| 6-261777 | 9/1994 | Japan | C12P 17/16 |
| 6-261778 | 9/1994 | Japan | C12P 17/16 |
| WO89-9827 | 10/1989 | WIPO | C12N 15/00 |
| WO92-19738 | 11/1992 | WIPO | C12N 15/31 |

OTHER PUBLICATIONS

Gibson, "Assay of Enzymes of Aromatic Metabolism", Methods in Microbiol.; 6B, pp. 463–478 (1977).
Wackett et al., "Survey of Microbial Oxygenases: Trichloroethylene Degradation by Propane–Oxidizing Bacteria", vol. 55, No. 11, pp. 2960–2964 (1989).
Krumme, et al., "Degradation of Trichloroethylene by . . . in Aquifer Microcosms", Appl. & Envir. Microb. (1993) 59 8, 2746–49.
Negoro et al., "Growth of Microalgae. . . . and $NO_x$", Appl. Biochem. and Biotech., vols. 28/29, 1991, pp. 877–886.
Nakajima et al., "Novel Metabolite. . . . Pathway", Biosci., Biotech. Biochem., 56 (3), 486–489, 1992.
Nakajima et al., Purification and Properties . . . Methylocystis, Biosci. Biotech. Biochem., 56 (5), 736–740, (1992).
"Preprint Extended Abstract", Hanson et al., "Development of Methantrophs", Div. Envir. Chem., ACS, 9/10–15, 1989, pp. 365–367.
Uchiyama et al., "Aerobic Degradation of . . . Strain M", Agr. Biol. Chem. 53 (11), 2903–2907, 1989.
Winter et al.,"Efficient Degradation . . . *E. Coli*", Bio. Technology, vol. 7, Mar. 1989, pp. 282–285.
Embley et el., "*Lactobacillus vaginales* . . . " Int. J. System Bact. vol. 39 (3) 368–370 (Jul. 1989).
Journal of Japan Sewage Works Association, vol. 24, No. 273, 1987/2, pp. 27–32.
Ewers et al., "Selection of . . . by TCE", Arch. Microbiol., vol. 154, No. 4, pp. 410–413 (1990).
Beam et al., "Microbial Degradation . . . ", J. Gen. Microbiol. 82, 163–169 (1974).
Little et al., Trichloroethylene Biodegradation . . . Bacterium, Appl. & Envir. Micro., vol. 54, No. 4, Apr. 1988, pp. 951–956.
Vandenbergh et al., "Metabolism of Volatile . . . *Pseudomonas fluorescens*", Appl. & Envir. Micro. vol. 54, No. 10, Oct. 1988, pp. 2578–2579.
Sandt et al., "Mobilization of the . . . in Drinking Water", Appl. & Environ. Micro., vol. 57, No. 1, Jan. 1991, pp. 194–200.
Kamath et al., "New Pathway . . . niger", Appl. & Envir. Micro., vol. 56, No. 1, Jan. 1990, pp. 275–280.
Shields et al., "Selection of *Pseudomonas cepacia* . . . ", Appl. & Environ. Microbiol. 58, 12, 3977–3983 (1983).
Vannelli et al., "Degradation of Halogenated Aliphatic . . . europea", Appl. & Envir. Micro., vol. 56, No. 4, Apr. 1990, pp. 1169–1171.
Harker, et al., "Trichloroethylene . . . JMP134", Appl. & Envir. Micro., vol. 56, No. 4, Apr. 1990, pp. 1179–1181.

(List continued on next page.)

*Primary Examiner*—David M. Naff
*Assistant Examiner*—Deborah K. Ware
*Attorney, Agent, or Firm*—Fitzpatrick, Cella, Harper & Scinto

[57]   ABSTRACT

A bacterium strain JM1 (FERM BP-5352) capable of degrading organic compounds without inducers is disclosed. Further, methods for degrading organic compounds and remedying an environment using the bacterium strain are also disclosed. The microorganism is brought into contact with the environment under conditions which stimulates the organism to degrade the organic compounds and thus, remedying the environment of pollutants. A kit and method for selectively detecting the strain expressing oxygenase from a sample containing strain J1 FERM BP-5102 is also disclosed. The latter strain expresses oxygenase when induced, however, strain JM1 FERM BP-5352 does not require induction. In addition, a process for obtaining strain JM1 FERM BP-5352 is also disclosed.

35 Claims, 8 Drawing Sheets

OTHER PUBLICATIONS

Vandenbergh et al., "Metabolism of Volatile . . . *Pseudomas fluorescens*", Appl. & Envir. Micro,m vol. 54, No. 10, Oct. 1988, pp. 2578–2579.

Tsien et al., "Biodegradation . . . OB3b", Appl. Envir. Micro., vol. 55, No. 12, Dec. 1989, pp. 3155–3161.

Nelson et al.,"Aerobic Metabolism . . . Isolate", Appl. & Envir. Micro., vol. 52, No. 2, Aug. 1986, pp. 383–384.

Nelson et al., "Biodegradation of Trichloroethylene . . . Pathway", Appl. & Envir. Micro., vol. 53, No. 5, May 1987, 949–954.

Wackett et al., "Degradation of Trichloroethylene . . . *Pseudomonas putida* F1", Appl. & Envir. Micro., vol. 54, No. 7, Jul. 1988, pp. 1703–1708.

Henry et al., "Influence of Endogenous . . . Groundwater Aquifer", Appl. & Envir. Microb., vol. 57, No. 1, Jan. 1991, pp. 236–244.

OXYGENASE EXPRESSING MICROORGANISM STRAIN JM1 (FERM BP-5352) FOR DEGRADING ORGANIC COMPOUNDS WITHOUT AN INDUCER

BACKGROUND OF THE INVENTION

1. Field of the Invention

The present invention relates to a novel microbial strain capable of degrading organic compounds, and to a process for degrading organic compounds and remedying environment using the same.

The present invention also relates to a process for obtaining a microorganism constitutively expressing oxygenase, and remedying environment using the microorganism obtained thereby.

The present invention also relates to a process for detecting a microorganism constitutively expressing oxygenase.

2. Related Background Art

Recently, a great problem has been an environmental pollution by chlorinated organic compounds which are harmful to organisms and difficult to degrade. Especially the soil in the manufacturing area of paper and pulp industry and semiconductor industry in Japan as well as abroad is considered to be contaminated with chlorinated organic compounds such as tetrachloroethylene (PCE), trichloroethylene (TCE), dichloroethylene (DCE) and the like. Actually there have been many reports on detection of such chlorinated organic compounds through environmental surveys.

It is supposed that chlorinated organic compounds remaining in soil dissolves in groundwater via rainwater etc. thus spread over the area. There is a strong suspicion that these compounds are carcinogens, and further, these are quite stable in the environment; therefore contamination of groundwater, which is used as a source of drinking water, is a serious social problem.

Thus purification of an aqueous medium such as groundwater, soil, and gas phase surrounding them to remove and degrade chlorinated organic compounds, is a very important problem in view of the protection of environment, and techniques needed for the purification have been sought to develop.

Recently, microbial degradation of these compounds has been reported as one of the techniques for purifying the environment contaminated with such chlorinated organic compounds, and various studies have started to put the process to a practical use. The advantages of the biodegradation process utilizing a microorganism includes degradation of chlorinated organic compounds into harmless substances by using an appropriately selected microorganism, no requirement for any special chemicals, and reduction of the labor and costs of maintenance.

The examples of strains capable of degrading TCE are given as follows:
*Welchia alkenophila* sero 5 (U.S. Pat. No. 4,877,736, ATCC 53570), *Welchia alkenophila* sero 33 (U.S. Pat. No. 4,877,736, ATCC 53571), Methylocystis sp. strain M (Agric. Biol. Chem., 53, 2903 (1989), Biosci. Biotech. Biochem., 56, 486 (1992), ibid. 56, 736 (1992)), *Methylosinus trichosporium* OB3b (Am. Chem. Soc. Natl. Meet. Dev. Environ. Microbiol., 29, 365(1989), Appl. Environ. Microbiol., 55, 3155 (1989), Appl. Biochem. Biotechnol., 28, 877 (1991), Japanese Laid-Open Patent Application (JPUPA) 02-92274, JPUPA 03-292970), Methylomonas sp. MM2 (Appl. Environ. Microbiol., 57, 236 (1991)), *Alcaligenes denitrificans* ssp. xylosoxidans JE75 (Arch. microbiol., 154, 410 (1990)), *Alcaligenes eutrophus* JMP134 (Appl. Environ. Microbiol., 56, 1179 (1990)), *Mycobacterium vaccae* JOB5 (J. Gen. Microbiol., 82, 163 (1974), Appl. Environ. Microbiol., 55, 2960 (1989), ATCC 29678), *Pseudomonas putida* BH (Journal of Japan Sewage Work Assosiation, 24, 27 (1987)), Acinetobactor sp. strain G4 (Appl. Environ. Microbiol., 52, 383 (1986), ibid. 53, 949(1987), ibid. 54, 951 (1989), ibid. 56, 276(1990), ibid. 57, 193 (1991), U.S. Pat. No. 4,925,802, ATCC 53617, this strain was originally classified as *Pseudomonas cepacia* then classified into Acinetobactor sp.), *Pseudomonas mendocina* KR-1 (Bio/Technol., 7, 282 (1989)), *Pseudomonas putida* F1 (Appl. Environ. Microbiol., 54, 1703 (1988), ibid. 54, 2578 (1988)), *Pseudomonas fluorescens* PFL12 (Appl. Environ. Microbiol., 54, 2578 (1988)), *Pseudomonas putida* KWI-9 (JPUPA 06-70753), *Pseudomonas cepacia* KK01 (JPUPA 06-22769), Pseudomonas sp. (JPUPA 02-273599), *Nitrosomonas europaea* (Appl. Environ. Microbiol., 56, 1169 (1990)), *Lactobacillus vaginalis* sp. nov (Int. J. Syst. Bacteriol., 39, 368 (1989), ATCC 49540) and so on.

All these strains, however, require a chemical substance such as aromatic compounds and methane as an inducer in order to express their TCE degrading activity.

For example, when the above microorganisms are used for degrading TCE, aromatic compounds such as phenol and toluene are very effective as an inducer. On the other hand, such compounds themselves are contaminants to environment; therefore considering the release into the environment, a complicated operation and monitoring are required. Methane can also serve as an effective inducer; but it is dangerous and difficult to introduce and control it in the environment because it is a flammable gas. Further, the inefficient degradation is another problem because the competitive antagonism occurs between the inducer and the substance subjected to degradation. The same problem occurs when chlorinated aromatic compounds such as PCP and PCB are degraded using a microorganism. The competitive antagonism also occurs between phenol and PCP, and biphenyl and PCB.

To overcome the above problems, Nelson et al. developed a process for degrading chlorinated organic compounds which uses tryptophan, an amino acid, as an inducer (Japanese Patent Application Laid-Open No.4-502277).

Although use of tryptophan allows us to avoid the problem of the toxicity and danger of the inducer itself, tryptophan is very expensive, and the intricacy of introduction and following control of a specific substance in the environment still remains.

Further, the enzyme activity of a TCE degrading enzyme such as oxygenase, expressed with an inducer, is normally maintained for only several hours to one day, and after that, successive addition of the inducer is required, which may cause competitive inhibition in TCE degradation.

Attempts have been made to introduce into a host bacterium a plasmid containing a DNA fragment encoding oxygenase, a TCE degrading enzyme, so that the bacterium will express TCE degrading activity with a harmless inducer or constitutively express it without any inducer. The bacterial strain from which the DNA fragment originates includes *Pseudomonas mendocina* KR-1 (Japanese Patent Application Laid-Open No.2-503866), *Pseudomonas putida* KWI-9 (Japanese Patent Application Laid-Open No.6-105691) and *Pseudomonas putida* BH (Proceedings of the 3rd Meeting of Assembly for study of groundwater/soil contamination and of countermeasures against it, p.213 (1994)).

There are various problems for such a recombinant, for example, requirement for IPTG (isopropyl thiogalactopyranoside), a very expensive substance, as an inducer, or insufficient stability of the plasmid in the host strain. Furthermore, from the viewpoint of public acceptance, release of a recombinant strain into an environment will be inevitably restricted.

Seales et al. made another attempt, that is, Acinetobactor sp. G4 (reclassified from *Pseudomonas cepacia* G4 to Acinetobactor sp. strain G4 when deposited in ATCC) was mutagenized using a transposon to obtain a strain constitutively expressing oxygenase necessary for TCE degradation (Appl. Environ. Microbiol., 58, p.3977 (1992), WO 92/19738).

This mutant derived from strain G4, however, does not have a sufficient TCE degradation activity, and its stability is questionable because of the transposon. Further, the transposon itself contains resistant markers such as kanamycin resistance, which causes a problem that it may undesirably affect other microorganisms through horizontal transfer when it is released into an environment.

As mentioned above, conventional microorganisms which require no inducer for degrading activity had to be selected by skilled experts using expensive equipments, and they are still not satisfactory in the degradation activity of contaminants.

SUMMARY OF THE INVENTION

It is an object of the present invention to provide a new microorganism capable of efficiently degrading organic compounds without any inducer.

Another object of the present invention is to provide a process for degrading organic compounds using a novel microorganism which is capable of degrading organic compounds without any inducer and is easy to obtain, and a process for remedying environment using the same.

It is a further object of the present invention to provide a process for obtaining a microorganism capable of degrading organic compounds without any inducer.

It is another object of the present invention to provide a process for detecting a microorganism capable of degrading organic compounds without any inducer.

One embodiment of the present invention provides a bacterium strain JM1 (FERM BP-5352) which is capable of degrading organic compounds without any inducer.

Another embodiment of the present invention is a process for degrading organic compounds using a microorganism constitutively expressing oxygenase, wherein the microorganism is obtained by mutagenizing with a mutagen an oxygenase-inducible microorganism.

Still another embodiment of the present invention is a process for remedying environment, comprising a step of degrading contaminants in an environment using a microorganism constitutively expressing oxygenase, wherein the microorganism is obtained by mutagenizing with a mutagen an oxygenase-inducible microorganism.

A further embodiment of the present invention is selective acquisition of a microorganism constitutively expressing oxygenase from an environment where the microorganism constitutively expressing oxygenase is present with a second microorganism having inducible oxygenase and an inducer capable of inducing oxygenase in the second microorganism, comprising the steps of:

providing a mixture of the above first microorganism constitutively expressing oxygenase and the above second microorganism having inducible oxygenase;

culturing the mixture on a culture medium containing a precursor which forms an oxide having detectable characteristics when oxidized by oxygenase and also functions as an inducer to allow colony formation, and isolating a colony which shows no substantial time lag between the growth of the microorganism and the formation of the oxide.

Another embodiment of the present invention is a process for selectively detecting the microorganism constitutively expressing oxygenase from an environment where a first microorganism constitutively expressing oxygenase is present with a second microorganism having inducible oxygenase and an inducer capable of causing the second microorganism to express oxygenase, comprising the steps of:

providing a mixture of the above first microorganism constitutively expressing oxygenase and the above second microorganism having inducible oxygenase;

providing a culture medium containing a precursor which forms oxide having detectable characteristics when oxidized by oxygenase and also functions as an inducer, and a nutrient which can support the growth of the microorganisms so as to form colonies some of which show no substantial time lag and the other shows substantial time lag between the growth of the colony and the indication of the formation of an oxide in the colony, when the mixture is cultured on the culture medium; and detecting the colony showing no substantial time lag between the growth of the colony and the formation of the oxide in the colony, after culturing the mixture on the culture medium to allow the colony formation for the microorganisms.

Another embodiment of the present invention is a process for selectively obtaining a microorganism inherently having a capacity for degrading organic compounds from an environment where a first microorganism inherently expressing a enzyme for degrading organic compounds is present with a second microorganism capable of inducibly expressing the enzyme, comprising the steps of:

providing a mixture of the first microorganism and the second microorganism; and culturing the mixture on a culture medium containing a precursor which forms a substance having detectable characteristics when subjected to the enzyme action and is also an inducer, so as to allow colony formation of the microorganisms; and isolating the microorganism showing no substantial time lag between its growth and formation of the product of the enzyme action.

Another embodiment of the present invention is a process for selectively detecting a microorganism constitutively expressing an enzyme capable of degrading organic compounds, from an environment where a first microorganism constitutively expressing the enzyme capable of degrading organic compounds is present with a second microorganism capable of inducibly expressing the enzyme, comprising the steps of:

providing a mixture of the first microorganism and the second microorganism;

providing a culture medium containing a precursor which forms a substance having detectable characteristics when subjected to the enzyme action and also containing a nutrient capable of supporting the growth of the microorganisms so as to form colonies some of which show no substantial time lag and the other shows substantial time lag between the growth of the colony and the indication of the formation of an oxide in the colony, when the mixture is cultured on the culture medium; and detecting the colony showing no substantial time lag between the growth of the colony and the formation of the product of the enzyme action in the colony, after culturing the mixture on the culture medium to allow colony formation.

Another embodiment of the present invention is a kit for detecting a microorganism constitutively expressing oxygenase in an environment where a microorganism constitutively expressing oxygenase is present with a microorganism capable of inducibly expressing oxygenase, comprising a culture medium containing a substance which develops a color when oxidized by oxygenase and a nutrient capable of supporting the growth of the microorganisms to form colonies, some of which show no substantial time lag, and the other of which show substantial time lag between the growth of the colony and the formation of colored portion due to the product of oxidation in the colony, when the mixture of the microorganism constitutively expressing oxygenase and the microorganism capable of inducibly expressing oxygenase is cultured on the culture medium.

In the present invention, the terms "no substantial time lag between growth of a microorganism and formation of oxide of a precursor" means that the presence of an oxide can be confirmed at the very point when the presence of the microorganism is detected by a conventional means for detecting microorganisms.

Further, in the present invention, the terms "a microorganism constitutively expressing oxygenase" means a microorganism which does not need the contact of an additional organic compound to express oxygenase, for example in degradation of the specific compound by oxygenase action.

Still further, in the present invention, the terms "a microorganism constitutively expressing an enzyme capable of degrading organic compounds" means a microorganism which does not need contacting with an additional organic compound to express the enzyme, for example, in degradation of a specific organic compound by its enzyme action.

DETAILED DESCRIPTION OF THE PREFERRED EMBODIMENTS

Figure 1:
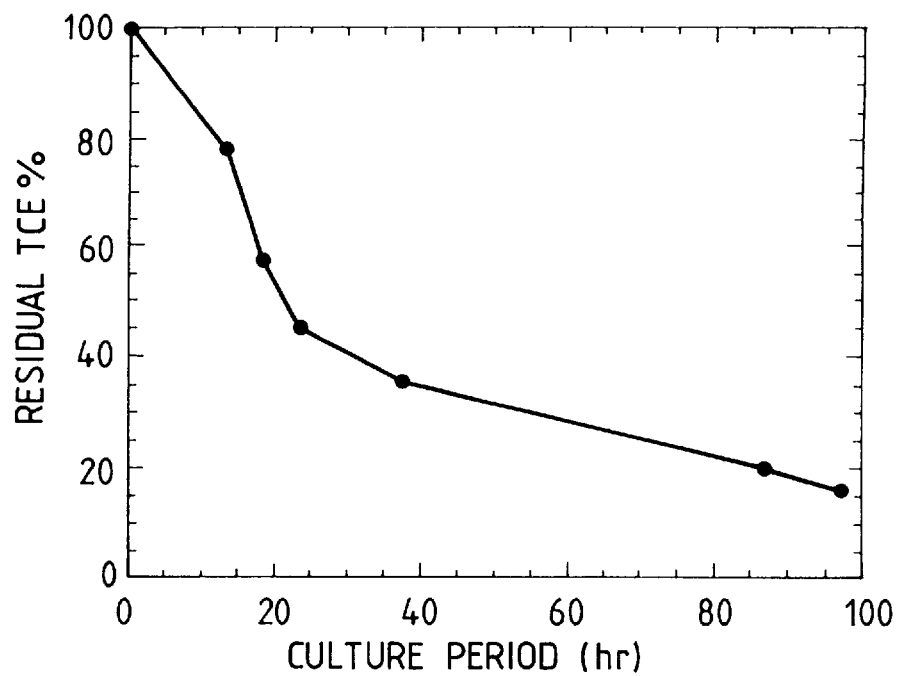
FIG. 1 is a graph showing TCE degradation in accordance with Example 8.

The present inventors have mutagenized with a mutagen a specific microorganism (International Deposit under Budapest Treaty, Accession Number: FERM BP-5102 deposited on May 25, 1994. /Identification Reference: Corynebacterium sp. J1, (the Identification Reference was renamed "J1", since it was found that the bacterium (FERM BP-5102) does not belong to genus Corynebacterium; hereinafter referred to as "strain J1")) which is capable of degrading aromatic compounds (phenol, toluene, cresol etc.) and chlorinated aliphatic hydrocarbon compounds with an inducer, to obtain a mutant strain capable of degrading these chemical substances without presence of any compounds such as known inducers, other than chemical substances to be degraded.

The present inventors also have found a process for remedying environment by bringing the mutant strain into contact with an environment (for example, aqueous medium, soil and gas phase) contaminated with aromatic compounds, chlorinated aliphatic hydrocarbon compounds and so on.

First, bacteriological characteristics of strain J1, which is a parent strain of the above mutant, are shown as follows:

Gram staining and morphology: Gram-negative rod
Growth condition in each medium
    BHIA: good
    MacConkey: possible
Color of colony: cream
Optimum growth temperature: 25° C.>30° C.>35° C.
Motility: negative (in semisolid medium)
TSI (slant/butt): alkali/alkali, $H_2S(-)$
Oxidase: positive (weak)
Catalase: positive
Fermentation of sugars
    glucose: negative
    sucrose: negative
    raffinose: negative
    galactose: negative
    maltose: negative
Urease: positive
Esculin hydrolysis (β-glucosidase): positive
Nitrate reduction: negative
Indole productivity: negative
Glucose acidification negative
Arginine dihydrase: negative
Gelatin hydrolysis (protease): negative
β-galactosidase: negative
Assimilation of each compound
    glucose: negative
    L-arabinose: negative
    D-mannose: negative
    D-mannitol: negative
    N-acetyl-D-glucosamine: negative maltose: negative
potassium gluconate: negative
n-capric acid: positive
adipic acid: negative
dl-malic acid: positive
sodium citrate positive
phenyl acetate: negative Strain J1 is capable of degrading chlorinated organic compounds and assimilating aromatic compounds, where oxygenase participates in the degradation. Its degradation activity is so high as to degrade about 20 ppm of TCE almost completely even at a low temperature of 15° C., which is close to the temperature of natural environment such as soil. It, however, requires an inducer of an aromatic compound such as phenol, toluene and cresol when degrading chlorinated organic compounds.

The mutant according to the present invention is the same as the above-mentioned strain J1 in bacteriological characteristics, while it is capable of degrading chlorinated organic compounds without aromatic compounds such as phenol, toluene and cresol as an inducer. Thus the present inventors recognized the mutant as a novel strain, and deposited it on Jan. 10, 1995 in National Institute of Bioscience and Human-Technology, Agency of Industrial Science and Technology (Deposit No.: FERM BP-5352). This strain was also first thought to belong to genus Corynebacterium, but it was found that the parent strain does not belong to genus Corynebacterium. Therefore, the Identification Reference for the strain (FERM BP-5352) was renamed. Hereinafter the novel strain is referred to as "strain JM1".

Strain JM1 can also degrade aromatic compounds such as phenol and cresol, and naturally resistant to such compounds. These chemicals are harmful to many microorganism as known from that they are usually used as disinfectants, and often contained in liquid wastes. strain JM1 can degrade chlorinated organic compounds even in the circumstance containing these chemical substances, without being killed or losing the degrading activity.

Further, when chlorinated organic compounds in the environment such as in groundwater and soil are to be degraded, supplement of an inducer such as phenol is not required by strain JM1 but only normal nutrients. Accordingly the manipulation becomes simpler and easier, and the problem of discharging a highly toxic and harmful inducer into the environment can avoided.

Still further, when chlorinated aliphatic hydrocarbon compounds, for example, is degraded by a microorganism which inducibly expresses oxygenase, an inducer such as phenol etc. has to be added and the induced oxygenase degrades both the inducer and chlorinated aliphatic hydrocarbon compounds, which results in the significant reduction of degradation efficiency of chlorinated aliphatic hydrocarbon compounds (competitive inhibition).

On the other hand, a microorganism constitutively expressing oxygenase does not require any inducer, and therefore, it can efficiently degrade chlorinated aliphatic hydrocarbon compounds.

To culture strain JM1 of the present invention, any ordinary carbon source, nitrogen source, and inorganic salts can be used as the nutrient in the culture medium so long as JM1 can assimilate them. For example, M9 medium supplemented with a small amount of yeast extract as a nutrient is applicable.

The following is the composition of M9 medium.
$Na_2HPO_4$: 6.2 g
$KH_2PO_4$: 3.0 g
NaCl: 0.5 g
$NH_4Cl$: 1.0 g (in 1 liter; pH 7.0)

Strain JM1 can be cultured under aerobic conditions, and both liquid culture and solid culture are applicable. Desirably the culture temperature is about 30° C.

Next, a process for obtaining the above mutant, strain JM1, is explained.

Strain JM1 can be obtained through an ordinary procedure, that is, by mutagenizing strain J1 using a mutagen.

As the mutagen, well-known physical and chemical mutagens can be used; for example, as a physical mutagen ultraviolet, as a chemical mutagen ethylmethanesulfonate, N-methyl-N'-nitro-N-nitrosoguanidine, nitrous acid or acridine dye can be used.

By using the above mentioned ordinary mutagenization method, microorganisms constitutively expressing oxygenase can be obtained more easily than with genetic recombination techniques, and its application range in environment remediation is much wider; therefore it is much more preferred.

Incidentally, the present inventors have found a novel technique in obtaining strain JM1 from the parental strain J1.

It concerns a process for selectively obtaining strain JM1 constitutively expressing oxygenase from an environment where both oxygenase-constitutive strain JM1 and oxygenase-inducible strain J1 are present.

A known trichloroethylene-degrading bacterium not requiring an inducer was obtained by picking up colored colonies on a culture medium containing compounds which forms a colored oxide when oxidized by oxygenase (hereinafter referred to as a precursor).

In particular, for example, the above-mentioned mutant of strain G4 was obtained taking advantage of yellow 7,7,7-trifluoro-2-hydroxy-6-oxo-2,4-heptadienoic acid (TFHA), which is an oxidation product of 3-trifluoromethylcatechol. The above mentioned genetic recombinant of stain KWI-9 was picked up taking advantage of indigo coloring blue, which is an oxidation product of indole. by the way, taking advantage of such characteristics of oxygenase for aromatic compounds, an industrial production of indigo from indole has been developed (Japanese Patent Application Laid-Open No. 6-261776, Japanese Patent Application Laid-Open No. 6-261777, Japanese Patent Application Laid-Open No. 6-261778).

After careful investigations, the present inventors have found that known precursors including the above-mentioned compounds all act as an inducer for a microorganism which inducibly expresses oxygenase.

This causes a problem when an oxygenase-constitutive microorganism is selectively picked up from an environment where oxygenase-constitutive and oxygenase-inducible microorganisms, for example strain JM1 and strain J1, coexist.

Apparently, this problem have not been recognized, because in the prior art the oxygenase-constitutive microorganism and oxygenase-inducible microorganism do not coexist during the isolation process.

Thus, there has been no guide for efficiently and selectively obtaining an oxygenase-constitutive microorganism from an environment where the oxygenase-constitutive microorganism and an oxygenase-inducible microorganism coexist.

After careful studying the above findings, the present inventors have found that there is a significant difference in the time lags, that is, between the growth of the microorganism and the appearance of the colored portion in the colony, of oxygenase-constitutive and oxygenase-inducible strains, which can be utilized to selectively obtain a microorganism constitutively expressing oxygenase.

Particularly explained with blue color development due to the oxidation of indole to indigo, cultured on an agar medium containing indole, an oxygenase-inducible microorganism develops color after the microorganism has formed a colony to some extent, at the center portion of the colony, and then gradually over the entire colony, while an oxygenase-constitutive microorganism develops color with the formation of a colony. Therefore, by examining the colonies for color development at a predetermined point of time before which only the oxygenase-constitutive microorganism can develop color, the oxygenase-constitutive microorganism can be selectively and efficiently obtained.

More particularly, for example, when strain J1 and strain JM1 were cultured at 30° C. on M9 agar medium containing indole as a precursor and 0.1% of yeast extract as a nutrient, both strain J1 and strain JM1 formed colonies of about 1–2 mm in diameter after one day culture. In the colonies of strain JM1, blue color of indigo, an oxide of indole, was observed all over the colony. On the other hand, in the colonies of strain J1, blue color of indigo was not observed with the eye. After 2–3 day culture, the colonies of both strains became about 5 mm in diameter. The entire portion of the colony of strain JM1 was blue with indigo, but in the colony of strain J1, a blue portion of 1–2 mm in diameter was observed just around the center of the colony.

The results show that it is possible to selectively obtain strain JM1 by picking up the colony showing no time lag between the growth of the microorganism and the appearance of the oxide of the precursor.

In the above process of selectively obtaining a microorganism constitutively expressing oxygenase, not only the compounds which form a colored oxide but also the ones which form a fluorescent oxide when oxidized by oxygenase are applicable as a precursor.

When a compound which forms a colored oxide detectable with the eye is used as a precursor, formation of the oxide to be utilized for selectively obtaining a microorganism constitutively expressing oxygenase, can be confirmed by the development of a color portion in the colony on a solid culture medium, for example, an agar medium as mentioned above.

When a compound which forms a fluorescent oxide is used as a precursor, the precursor added to a liquid culture medium is taken in by the cultured microorganism, and oxidized by oxygenase, which leads to color (fluorescence) development of the cell. The color (fluorescence) development can be detected by cell detection means, such as a flow cytometer (FCM), a fluorescence microscope and so on to isolate the desired microorganism. In this case, because the cell growth period such as colony formation is not required, the process is more efficient. To be more detailed, when indole is used as a precursor, green fluorescence of indoxyl, an intermediate product during oxidization of indole into indigo by oxygenase, can be utilized.

A precursor used for the process for selectively obtaining a microorganism constitutively expressing the above-mentioned oxygenase is preferably selected according to the type of oxygenase of the targeted microorganism.

In the case of the above strain JM1, for example, indole, creosote, catechol, 3-methylcatechol, 3-trifluoromethylcatechol and o-aminophenol are preferably used as a precursor, because the strain constitutively expresses aromatic compound oxygenase which degrades organic compounds, for example aromatic compounds and chlorinated aliphatic hydrocarbon compounds, through a degradation pathway for aromatic compounds.

When oxygenase is an alkane compound oxygenase or an ammonia oxygenase, a precursor suitable for each oxygenase may be applied.

The above-mentioned process for obtaining a microorganism constitutively expressing oxygenase also has other uses.

For example, as an application of a microorganism constitutively expressing oxygenase, the microorganism may be put into an environment contaminated with contaminants to remedy the environment, and for efficient remediation, a continued monitoring of the microorganism in the environment is very important. Therefore, required is a technique to detect exclusively the microorganism constitutively expressing oxygenase among various native microorganisms in the environment. Here, above process can be used to selectively detect the microorganism constitutively expressing oxygenase in the environment to be remedied.

In particular, the detection of the presence of the microorganism constitutively expressing oxygenase in the environment undergoing remediation is done by detecting a microorganism which does not show substantial time lag between its growth and the formation of an oxide of a precursor when a mixture of microorganisms obtained from the environment are cultured on a culture medium containing a precursor.

In case of utilizing a difference between the two time lags for detecting in an environment a microorganism constitutively expressing oxygenase, one of the time lag between growth and oxide production, e.g. the development of a colored portion in a culture of an oxygenase-constitutive microorganism, and another time lag is between the growth and oxide production, e.g. the development of a colored portion in a culture of a microorganism inducibly expressing oxygenase, it is preferable that a mixture of microorganisms obtained from the environment is first cultured in a culture medium containing no inducer to diminish the expressed oxygenase activity in microorganisms, prior to the aforementioned step of culturing on a culture medium containing the precursor, because there may be certain native microorganisms inducibly expressing oxygenase in the environment.

In the above-mentioned process for selectively obtaining the microorganism constitutively expressing oxygenase and process for detecting the same using the above process, nutrients are preferably added to the culture medium to allow equal growth rate for both the microorganism constitutively expressing oxygenase and the microorganism inducibly expressing oxygenase.

It enables easy comparison of time lags between growth of each microorganism and formation of oxide of a precursor in the culture between the microorganism constitutively expressing oxygenase and the microorganism inducibly expressing oxygenase.

When the above-mentioned strain JM1, which is a mutant of strain J1, is obtained from an environment where JM1 and strain J1 coexist, selection of nutrient is not important because, in general, there might not be a significant difference between the growth rates of the parent strain and the daughter strain.

However, when detecting a microorganism constitutively expressing oxygenase in an environment to be remedied, selection of nutrient is more important since it may affect the precision of detection because of the various kinds of microorganisms present in the environment.

Thus, when the process for detecting a microorganism constitutively expressing oxygenase in an environment which undergoes remediation is carried out, it is preferable that prior to the detection, for example, the growth rates of both the microorganism constitutively expressing oxygenase and the microorganisms in the environment which undergoes remediation in response to various nutrients are determined, to select nutrient so as to give approximately the same growth rate, and then the selected nutrient is added to the culture medium.

The culture medium to be used may vary according to the microorganisms inhabiting each environment which undergoes remediation and should not be determined sweepingly. A culture medium suitable for each environment which undergoes remediation can be selected from, for example, natural media such as yeast extract, peptone, broth and malt extract, and synthetic media which are inorganic salt media supplemented with carbon source and energy source.

Microorganisms constitutively expressing oxygenase which can be detected by the above process are not limited to those which are mutagenized with mutagen, such as the above-mentioned strain JM1. Known microorganisms constitutively expressing oxygenase, for example, recombinants of *Pseudomonas mendocina* KR-1, can be also detected.

Explanation will be given to a process for degrading organic compounds and for remedying an environment both of which use a microorganism constitutively expressing oxygenase.

The process for degrading organic compounds, for example, aromatic compounds (phenol, toluene, cresol etc.) and chlorinated aliphatic hydrocarbon compounds (trichloroethylene, dichloroethylene etc.), using a microorganism constitutively expressing oxygenase, for example, the microorganism obtained by the above-mentioned process (strain JM1 etc.) can be carried out by bringing the organic compounds in contact with the microorganism. The process does not require any inducer before and throughout the degradation treatment.

Any method is applicable to contacting the microorganism with the targeted organic compounds, as long as conditions are normal ones under which the microorganism can exhibit its degradation activity. Batch method, semi-continuous method and continuous method etc. are applicable. The microorganism can be utilized in a semi-immobilized state or in such a state that it is immobilized to a suitable carrier.

Bringing the microorganism according to the present invention which constitutively expresses oxygenase in contact with a liquid medium containing organic compounds which are contaminants, such as aromatic compounds (phenol, toluene, cresol etc.) and chlorinated aliphatic hydrocarbon compounds (trichloroethylene, dichloroethylene, etc.) makes it possible to degrade the above organic compounds and purify the above liquid media.

The main uses are shown below, but are not intended to limit the present invention. The present strain is applicable to any purification treatment for liquid media contaminated with organic compounds.

The easiest and simplest use is such that strain JM1 is directly introduced into a liquid medium contaminated with, for example, aromatic compounds and chlorinated aliphatic hydrocarbon compounds. In this case, it is necessary to adjust pH value, salt concentration, temperature, contaminant concentration etc. of the liquid medium, but degradation activity of strain JM1, for example, is maintained unless the liquid medium is extremely acid, alkaline or of high salt concentration. As mentioned above, it is capable of degrading TCE whose concentration is as high as 20 ppm. Further even at a temperature of 15° C., lower than ordinary culture temperature at a laboratory, it can grow sufficiently and its degradation activity can be maintained.

Another use is such that the microorganism is cultured in a culture vessel arranged beforehand, and then contaminated aqueous medium is introduced into the vessel at a given flow rate so as to undergo degradation treatment. Introduction and discharge of the liquid medium may be carried out continuously, or it may be carried out intermittently according to the degradation capacity, or a batch method is also applicable. Preferably such control is systematized in connection with the concentration of aromatic and/or chlorinated organic compounds to give optimum results.

Still another use is such that the microorganism is adhered to a carrier like soil particles, the carriers are charged into a reaction vessel, and then the contaminated liquid medium is introduced into the vessel to undergo degradation treatment. Besides particles of soil, any carrier can be used, however, it is desirable that those having an excellent retention of microorganisms and a stable gas permeability are employed. For example, applicable are various carriers of microorganisms which have been generally applied to bioreactors used in the drug manufacturing industry, the food industry, the liquid waste treatment system and so on, because they provide suitable habitats for microorganisms.

More particularly, inorganic particulate carriers, such as porous glass, ceramics, metal oxides, activated charcoal, kaolinite, bentonite, zeolite, silica gel, alumina, anthracite, and so on; gel carriers, such as starch, agar, chitin, chitosan, polyvinyl alcohol, alginic acid, polyacrylamide, carrageenan, agarose, gelatin, and so on; ion-exchange cellulose; ion-exchange resin; cellulose derivative; glutaric aldehyde; polyacrylic acid; polyurethane; polyester; and so on. The natural matter, for example, cotton, hemp, paper, etc. which are cellulosic; wood powder, bark, etc. which contain lignin; is also applicable.

According to the present invention, the degradation treatment for organic compounds which is contaminants in soil can be achieved by contacting the microorganism with the organic compounds in the soil. The main uses are shown below, but are not intended to limit the present invention. The present strain is applicable to various purification treatment for the soil contaminated with aromatic and/or chlorinated aliphatic hydrocarbon compounds.

The easiest and simplest use is such that the microorganism is directly introduced into soil contaminated with organic compounds which are contaminants, for example, aromatic and chlorinated organic compounds. Introduction of the microorganism may be carried out by spraying it on the surface of the soil and, when the treatment extends to deep underground, by introducing it through the well arranged in the underground.

Application of pressure of air, water, etc. allows the microorganism to spread over the wide area of the soil and makes the process more effective. In this case, it is necessary to adjust various conditions of the soil so that they are suitable for the microorganism used for the process. The growth of the microorganisms is quickened in the presence of carriers like soil particles, and therefore, it is very convenient that the process is carried out in soil. Further, the microorganism can grow even at the temperature of 15° C. which is normally thought to be the average temperature of soil, and can maintain its degradation activity.

Another use is such that first the microorganism is adhered to a carrier, next the carriers are charged into the reaction vessel, and then the reaction vessel is introduced into, primarily, the aquifer of the contaminated soil, to undergo degradation treatment.

The form of the reaction vessel is desirably like a fence or a film which can cover the wide area of the soil. Any carrier can be used, however, it is desirable that those having an excellent retention of microorganisms and a stable gas permeability are employed.

As a material of the carrier, which can provide suitable habitats for microorganisms, for example, the same materials as mentioned above are applicable.

According to the present invention, the degradation treatment for organic compounds which is contaminants in gas phase can be achieved by contacting the microorganism with the contaminants in the gas phase. The main uses are shown below, but are not intended to limit the present invention. The present strain is applicable to purification treatment for any aspect of gas phase contaminated with aromatic and/or chlorinated organic compounds.

One use is, for example, such that the microorganism is cultured in a culture vessel arranged beforehand, and then contaminated gas is introduced into the vessel at a given flow rate to undergo degradation treatment. The method of introducing the gas is not limited specifically, but it is desirably such that introduction of the gas causes agitation of the culture medium and promote its aeration. Introduction and discharge of the gas may be carried out continuously, or it may be carried out intermittently according to the degradation capacity. A batch method is also applicable. Preferably such control is systematized in connection with the concentration of chlorinated organic compounds to give optimum results.

Another use is such that the microorganism is adhered to a carrier like a particle of soil, the carriers are put into a reaction vessel, and then the contaminated gas is introduced into the vessel to undergo degradation treatment. Besides particles of soil, any carrier can be used, however, it is desirable that those having an excellent retention of microorganisms and a stable gas permeability are employed.

As a material of the carrier, which can provide suitable habitats for microorganisms, for example, the same materials as mentioned above for purification treatment of soil are applicable.

As materials which can retain the present strain and supply it with nutrient, many examples can be given from among the compost used in the agriculture, forestry and fisheries and allied industries. Specifically, dry materials from plants, such as straw of grains, sawdust, rice bran, bean curd lees, bagasse and so on, and seafood wastes, such as shells of crab and lobster and so on are applicable.

In purification of contaminated gas, the strain may be introduced before or after carrier material is added to the culture medium. To make the degradation reaction efficient, it is preferable that the above-mentioned nutrient, water content, oxygen concentration, etc. are kept in desirable conditions. The ratio of carrier to water in a reaction vessel may be determined considering the growth of the microorganism and gas permeability of the medium. The shape of the vessel may be selected considering the amount and concentration of the gas undergoing treatment, but preferably it is designed so that the contact of the gas with the microorganism held by the carrier may be enhanced. For example, column, tube, tank and box type are applicable. The vessel of these forms may be joined together with an exhaust duct and a filter to form one unit, or plural vessels may be connected in series or parallel according to the capacity.

Contaminated gas is sometimes adsorbed by carrier material in the beginning of the reaction and there is very few case where the effect of utilizing microorganism may not be exhibit. After a certain period of time, however, contaminants adhered to the carrier material is degraded, and further contaminants can be adsorbed by the surface of the material. Thus the adsorption of the material is thought to be restored, and it is presumed that the capacity of removing contaminants is not saturated and a certain amount of degradation activity is maintained.

As materials for growing the microorganism in the aforementioned purification treatment, the normal culture media used for culturing microorganisms are applicable. In the case of strain JM1, available media include, for example, bouillon medium, M9 medium, 2XYT medium, L medium, and the media in which polypeptone, yeast extract, etc. and carbon sources such as sugars and organic acids are mixed at an arbitrary ratio. These media can be liquid, or gel with addition of agarose.

The process for remedying environment as mentioned above is applicable to all the treatment of liquid wastes, soil and air, whether they are in an open system or a closed system. And the microorganism can be used in a state of being immobilized to a carrier, further, various methods for quickening the growth of the microorganism can be jointly used.

As illustrated above, according to one aspect of the present invention, it is possible to efficiently degrading organic compounds without using an inducer.

Further, according to one aspect of the present invention, it is possible to efficiently remedying an environment contaminated with organic compounds without affecting the environment so much.

Still further, according to one aspect of the present invention, it is possible to obtain and detect a microorganism constitutively expressing an enzyme.

A number of embodiments of the present invention will now be explained in more detail with reference to the following examples.

EXAMPLE 1
Isolation of Strain JM1 and Activity of Oxygenase Thereof

A colony of strain J1 (FERM BP-5102) on an agar medium was inoculated into 100 ml of M9 medium containing 0.1% of yeast extract and 200 ppm of phenol, followed by shaking culture in a Sakaguchi flask (a shouldered round flask) at 30° C. for 18 hours.

Then 10 ml of the above culture was centrifuged to collect the cells. After the supernatant was removed, was added 5 ml of M9 medium containing 20 ppm of NTG (N-methyl-N'-nitro-N-nitrosoguanidine) and 200 ppm of phenol followed by shaking culture at 30° C. After 2–3 hours of culture, when the culture medium started to be colored yellow, the color of 2-hydroxymuconic acid semialdehyde, an intermediate decomposition product of phenol, a portion of the culture was spread onto the M9 agar medium containing 200 ppm of indole and 0.1% of yeast extract, and incubated at 30° C.

Generally, various aromatic compound-degrading (oxidation or hydroxylation) enzymes convert indole into indigo which is blue in color.

After one day of culture, once could see colonies of 1–2 mm in diameter formed on the culture medium. Some colonies were entirely deep blue, and some remained in their original color (white). After 2–3 days of culture, almost all colonies grew to be about 5 mm in diameter. At this point, some were entirely deep blue, while the others were white except for a blue-colored portion of 1–2 mm of diameter in the center.

Then a colony which was entirely blue was inoculated into 200 ml of M9 medium supplemented only with 0.2% yeast extract in a Sakaguchi flask. After shaking culture at 30° C. for 24 hours, the culture was centrifuged to separate the cell pellet, which was then disrupted by a French press to obtain cell extract. Then the cell extract was used to detect the enzyme activities of catechol-1,2-oxygenase (C12O) and catechol-2,3-oxygenase (C23O) by spectroscopy (Methods in Microbiol,; 6B, 463–478 (1977)).

The determination of protein content was made using a Biorad protein assay kit. Enzyme activities of strain J1 under the same conditions as above and that of strain J1 cultured in the presence of 100 ppm phenol were also measured for comparison. The results are shown in Table 1.

Table 1. Specific Activities of C12O/C23O of strain J1 and a bacterium obtained in Example 1

| Enzyme<br>Strain | Specific Activity<br>($\mu$ mol/min. per mg protein) | |
|---|---|---|
|  | C12O | C23O |
| a bacterium obtained in Ex. 1 | 0.103 | 1.96 |
| strain J1 (without phenol) | 0.011 | 0.015 |
| strain J1 (with phenol) | 0.109 | 1.88 |

It is found from the results shown in Table 1 that the colored colony is a strain which shows an oxygenase activity stronger than that of strain J1 cultured in the presence of phenol (an inducer), thus it is inherently, or constitutively expressing oxygenase, differing from strain J1 in that point.

The bacteriological characteristics of the strain are shown below, and they are the same as strain J1.

Gram stain and morphological type: Gram-negative rod
Growth condition in each medium
  BHIA: good
  MacConkey: possible
Color of colony: cream
Optimum temperature: 25° C.>30° C.>35° C.
Motility: negative (semisolid medium)
TSI (slant/butt): alkali/alkali, $H_2S(-)$
Oxidase: positive (weak)
Catalase: positive
Fermentation of sugars
  glucose: negative
  sucrose: negative
  raffinose: negative
  galactose: negative
  maltose: negative
Urease: positive
Esculin hydrolysis ($\beta$-glucosidase): positive
Nitrate reduction: negative
Indole productivity: negative
Glucose acidification: negative
Argininedihydrase: negative
Gelatin hydrolysis (protease): negative
$\beta$-galactosidase: negative
Assimilation of each compound
  glucose: negative
  L-arabinose: negative
  D-mannose: negative
  D-mannitol: negative
  N-acetyl-D-glucosamine: negative
  maltose: negative
  gluconic acid potassium: negative
  n-capric acid: positive
  adipic acid: negative
  dl-malic acid: positive
  sodium citrate: positive
  phenyl acetate: negative As a result, it was confirmed that the above colored strain is a novel strain constitutively expressing oxygenase and a mutant derived from strain J1 by the action of mutagen. It was deposited in the following International Depositary Authority under the accession No. FERM BP-5352, in accordance with Budapest Treaty on the International Recognition of the Deposit of Microorganisms for the Purposes of Patent Procedure. 1-3, Higashi 1 chome Tsukuba-shi Ibaraki-ken 305, Japan National Institute of Bioscience and Human-Technology, Agency of Industrial Science and Technology Then fresh culture of strain J1 (FERM BP-5102) was inoculated into 100 ml of M9 medium containing 0.1% of yeast extract and 200 ppm of phenol in a Sakaguchi flask, followed by shaking culture at 30° C. for 18 hours.

Then 10 ml of the above culture medium was centrifuged to collect cells. After the supernatant was removed, was added 5 ml of M9 medium containing 20 ppm of NTG (N-methyl-N'-nitro-N-nitrosoguanidine) and 200 ppm of phenol to undergo shaking culture at 30° C. After 2–3 hours o culture, when the culture medium started to be colored yellow due to the color of 2-hydroxymuconic acid semialdehyde, an intermediate product of phenol, a portion of the culture medium was spread onto the M9 agar medium containing 200 ppm of indole and 0.1% of yeast extract, and incubated at 30° C.

After one day of culture, among the colonies formed on the culture medium, those which were entirely colored in deep blue were picked up by visual selection. With each colonies, oxygenase activity and the bacteriological characteristics were examined in the same manner as above. As a result, the microorganism was recognized to be strain JM1. In other words, strain JM1 was selectively obtained from the culture of strain J1, by selecting a strain whose growth and the expression of oxygenase started simultaneously, where there was time lag between the growth of strain J1 and the expression of oxygenase.

Selective Detection of Strain JM1 Using a Precursor (Examples 2–7)

EXAMPLE 2

Detection of Strain JM1 Using Catechol or Phenol

A colony of strain J1 on an agar medium and a colony of strain JM1 obtained as in Example 1 were inoculated into 100 ml of M9 culture medium containing 0.1% of yeast extract,respectively, followed by shaking culture in a Sakaguchi flask at 30° C. for 18 hours.

Both above cultures were was mixed and then p portion of the mixture was spread on M9 agar medium containing 0.1% of yeast extract and 200 ppm of catechol as a precursor to be oxidized, and incubated at 30° C.

Generally, various aromatic compound-degrading (oxidation or hydroxylation) enzymes convert catechol into yellow-colored hydroxymuconic acid semialdehyde (HMS) via metasplitting of the aromatic ring.

After one day culture, observed were colonies of 1–2 mm in diameter, some of which were entirely colored yellow and others remaining white. Then the colonies which were entirely yellow were picked up, and their characteristics were determined in the same manner as in Example 1. As a result, the colored colonies were confirmed to be strain JM1.

It was also observed that colonies of strain J1, which did not indicate the presence of oxygenase at the point of one day culture, became yellow in its center portion after two day culture.

The above results show that strain JM1 can be picked up from strain J1 taking advantage of the time lag between the growth of the microorganism and the expression of oxygenase.

The same results were obtained when phenol was used as an precursor.

EXAMPLE 3

Detection of Strain JM1 Using 3-methylcatechol or m-cresol

Cells of strain J1 and strain JM1 were cultured in the same manner as in Example 2 except that 3-methylcatechol was used instead of catechol as an precursor to be oxidized.

Normally 3-methylcatechol is converted into 2-hydroxy-6-ketohepta-2,4-dienoic acid (HOD) which is yellow via metasplitting of aromatic ring by various aromatic compound-degrading enzymes (oxidation or hydroxylation).

When strain J1 was grown on M9 agar medium containing 200 ppm of 3-methylcatechol and 0.1% of yeast extract, colonies of visible size were formed within one day culture, and a yellow-colored portion is developed, which indicates the presence of HOD, in the colony by two days of culture.

On the other hand, in the case of strain JM1, there was no time lag observed between the growth of the microorganism and the development of HOD, and the colony was yellow even at the point when the colony becomes just visible (within one day after the culture started). Thus, strain JM1 could be differentiated from strain J1 by selecting the yellow colony just at the point when the colony grew to be just visible size.

The same results were obtained when m-cresol instead of 3-methylcatechol was used as an precursor.

EXAMPLE 4

Detection of Strain JM1 Using 3-trifluoromethylcatechol or m-trifluoromethylphenol Cells of strain J1 and strain JM1 were cultured in the same manner as in Example 2 except that 3-trifluoromethylcatechol was used instead of catechol as an precursor to be oxidized.

Normally 3-trifluoromethylcatechol is converted into 7,7,7-trifluoro-2-hydroxy-6-oxo-2,4-heptadienoic acid (TFHA) which is yellow via metasplitting of the aromatic ring by various aromatic compound-degrading (oxidation or hydroxylation).

When strain J1 was cultured on M9 culture medium containing 200 ppm of 3-trifluoromethylcatechol and 0.1% of yeast extract, colonies of visible size were formed within one day culture, and a yellow-colored portion is developed, which indicates the presence of TFHA, in the colony by two days of culture.

On the other hand, in the case of strain JM1, there was no time lag observed between the growth of the microorganism and the development of THFA, and the colony was yellow even at the point when the colony becomes just visible (within one day after the culture started). Thus, strain JM1 could be differentiated from strain J1 by selecting the yellow colony just at the point when the colony grew to be just visible size.

The same results were obtained when m-trifluoromethylphenol instead of 3-trifluoromethylcatechol was used as an precursor.

EXAMPLE 5

Detection of Strain JM1 Using Creosote

Cells of strain J1 and strain JM1 were cultured in the same manner as in Example 1 except that creosote instead of catechol was used as an precursor to be oxidized.

Normally creosote is converted by various aromatic compound-degrading (oxidation or hydroxylation) enzymes to develop reddish purple color.

When strain J1 was cultured on M9 culture medium containing 200 ppm of creosote and 0.1% of yeast extract, colonies of visible size were formed within one day culture, and a reddish purple-colored portion is developed, which indicates the presence of creosote oxide, in the colony by two days of culture.

On the other hand, in the case of strain JM1, there was no time lag observed between the growth of the microorganism and the development of creosote oxide, and the colony was reddish purple even at the point when the colony becomes just visible (within one day after the culture started). Thus, strain JM1 could be differentiated from strain J1 by selecting the reddish purple colony just at the point when the colony grew to be just visible size.

EXAMPLE 6

Detection of Strain JM1 Using Indole by FCM

A colony of strain J1 and a colony of strain JM1 were respectively inoculated into 100 ml of M9 medium containing 0.1% of yeast extract, and cultured with shaking in a Sakaguchi flask at 30° C. for 18 hours as a preculture.

A 0.1 ml portion of each of the above cultures was added to 30 ml of M9 medium containing 0.1% yeast extract and 200 ppm of indole, which is a precursor to be oxidized, followed by shaking culture at 30° C.

When indole is converted into indigo by an aromatic compound-degrading (oxidation or hydroxylation) enzyme as mentioned above, an intermediate product, indoxyl, is formed during the process and emits green fluorescence.

When strain J1 was cultured in M9 medium containing 200 ppm of indole and 0.1% of yeast extract, cells began to emit green fluorescence due to indoxyl within 24 hours after the culture started.

On the other hand, in the case of strain JM1, the green fluorescence due to indoxyl was emitted around 10 hours after the culture started.

Then after the shaking culture for 10 hours, the both cultures were centrifuged to collect pellets, and the pellets were again dispersed in a sheath solution in a cell concentration of $10^5$–$10^6$ cells/ml separately. The number of the cells was measured by using a Facs-Can, an FCM manufactured by Becton Dickinson Co. As a result, concerning FSC (forward scattering) which depends on the cell size etc., equal peaks were obtained, but it was possible to differentiate strain JM1 from strain J1 by gating the channel spectrometrically detecting fluorescence of indoxyl at a given width of signal level of fluorescence histogram.

EXAMPLE 7

Detection and Isolation of Strain JM1 Using Indole by Fluorescence Microscopy

Each colony on an agar medium of strain J1 and strain JM1 obtained in accordance with Example 1 was inoculated into 100 ml of M9 culture medium containing 0.1% of yeast extract, and cultured with shaking in a Sakaguchi flask at 30° C. for 18 hours as a preculture.

A portion of 0.1 ml of each culture was added to 30 ml of M9 culture medium containing 0.15 yeast extract and 200 ppm of indole which is a precursor to be oxidized followed by shaking culture at 30° C. for 10 hours. The pellets collected from the culture by centrifugation were again dispersed in an M9 medium containing no carbon source to the concentration of $10^2$–$10^3$ cells/ml, and serial dilution was done in a 96 well microplate.

The specimens were subjected to fluorescence observation using an incident-light fluorescence microscope (IMT-2 manufactured by Olympus Optical Co., Ltd.).

The result that the cell which itself emitted green fluorescence presumably due to indoxyl, was strain JM1 and the cell which did not emit fluorescence was strain J1 was also confirmed by the color development of the colonies on an agar medium containing indole.

Degradation of Organic Compounds Using Strain JM1

(Examples 8–11)

EXAMPLE 8

Degradation of TCE Using Strain JM1 (Liquid Culture System)

A colony on an agar medium of strain JM1 obtained in accordance with Example 1 was inoculated into 200 ml of an M9 medium containing 0.2% of yeast extract in a Sakaguchi flask, and cultured with shaking at 30° C. for 24 hours.

Then vials each containing 5 ml of M9 medium containing 10 ppm of TCE and 0.1% of yeast extract as a carbon source were prepared and 0.1 ml of the culture prepared as above was inoculated into each vial.

After each vial was sealed with a butyl rubber stoppers and an aluminum cap, shaking culture was conducted at 30° C.

The quantity of TCE was determined at predetermined time intervals by head space gas chromatography. As a control, the same experiment was done except that strain JM1 was not added. Thus the percentage of the residual TCE quantity to the TCE quantity of the control was calculated. The results are depicted in FIG. 1.

EXAMPLE 9

Degradation of DCE Using Strain JM1 (Liquid Culture System)

Figure 2:
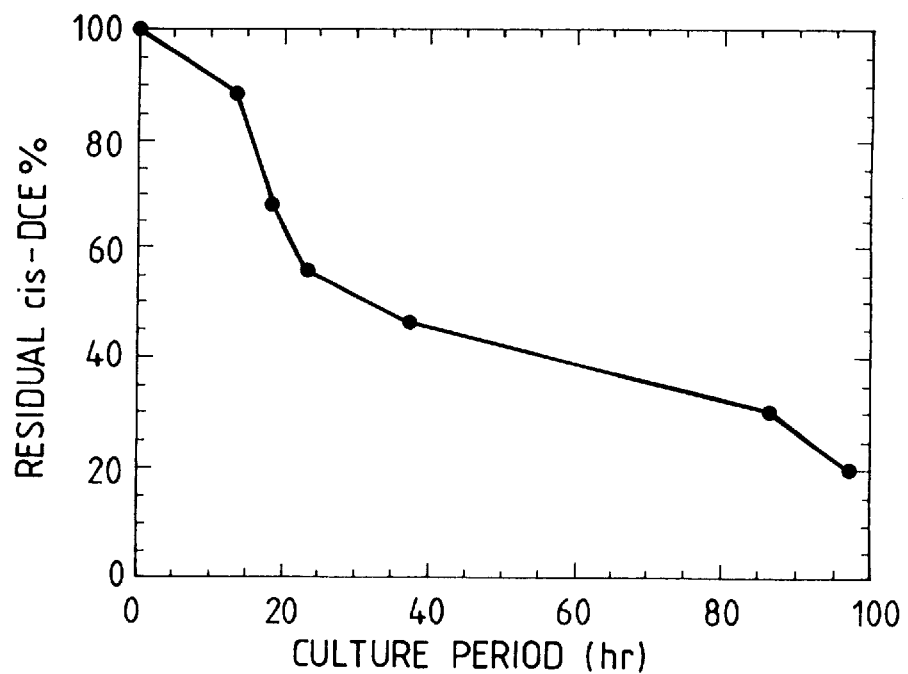
FIG. 2 is a graph showing cis-DCE degradation in accordance with Example 9.
Figure 3:
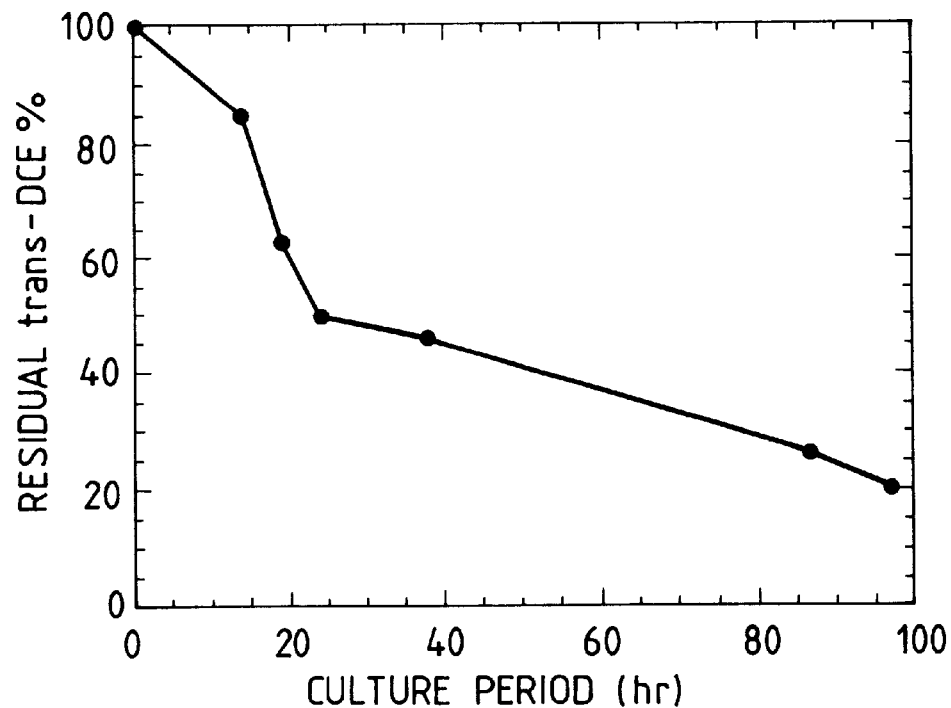
FIG. 3 is a graph showing trans-DCE degradation in accordance with Example 9.

Decrease of DCE was measured at predetermined time intervals in the same manner as in Example 8 except that the substances subjected to degradation were 10 ppm of cis-1,2-dichloroethylene (cis-1,2-DCE) and 10 ppm of trans-1,2-dichloroethylene (trans-1,2-DCE). And the percentage of the residual amount to the control amount was calculated for each substance. The results are depicted in FIG. 2 (cis-1,2-DCE) and FIG. 3 (trans-1,2-DCE).

EXAMPLE 10

Degradation of Aromatic Compounds Using Strain JM1 (Liquid Culture System)

Figure 4:
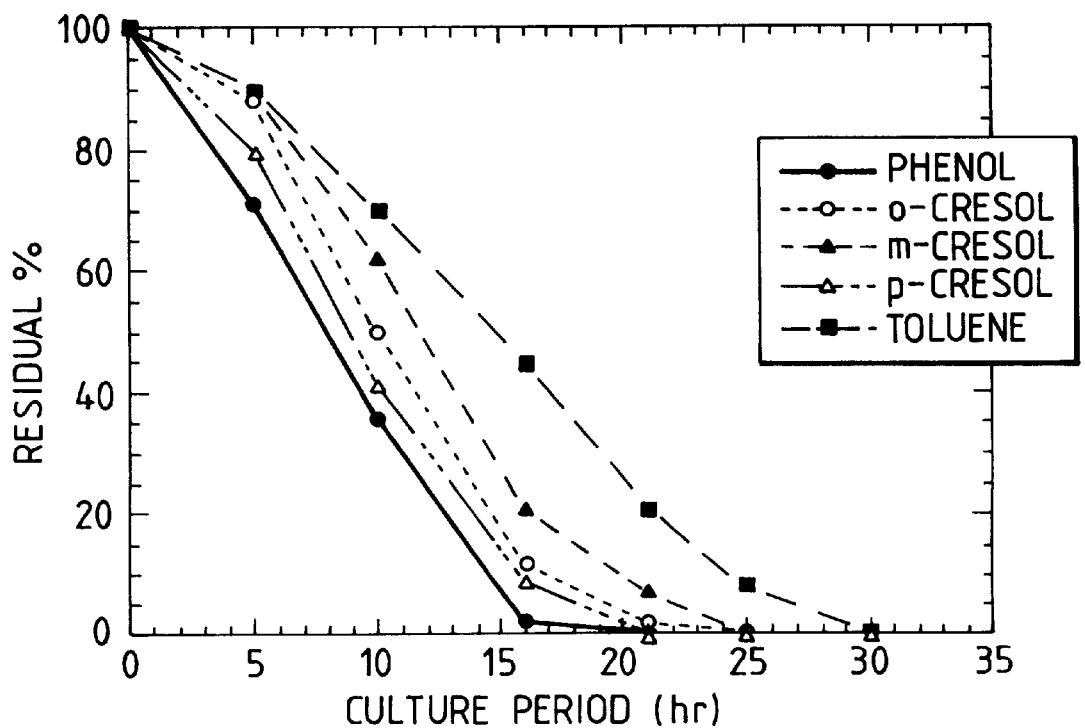
FIG. 4 is a graph showing the degradation of aromatic compounds in accordance with Example 10.

Decrease of each aromatic compound was measured along time in the same manner as in Example 8 except that the substances subjected to degradation were phenol (200 ppm), o-cresol (200 ppm), m-cresol (200 ppm), p-cresol and toluene (50 ppm). The measurements were made by liquid chromatography for phenol and cresol, and by gas chromatography for toluene. And the residual percentage of the aromatic compound to the control was calculated for each substance. The results are depicted in FIG. 4.

EXAMPLE 11

Comparison of Growth and TCE Degradation Between Strain J1 and Strain JM1

The following three groups were prepared, and microbial growth (cell number) and TCE degradation (concentration of residual TCE) were measured at predetermined time intervals in the same manner as in Example 8.

The cell number was determined by the plate count method and the quantity of TCE by gas chromatography. And as for the quantity of TCE, the percentage of the residual TCE to the TCE quantity of the comparative sample was calculated.

Figure 5:
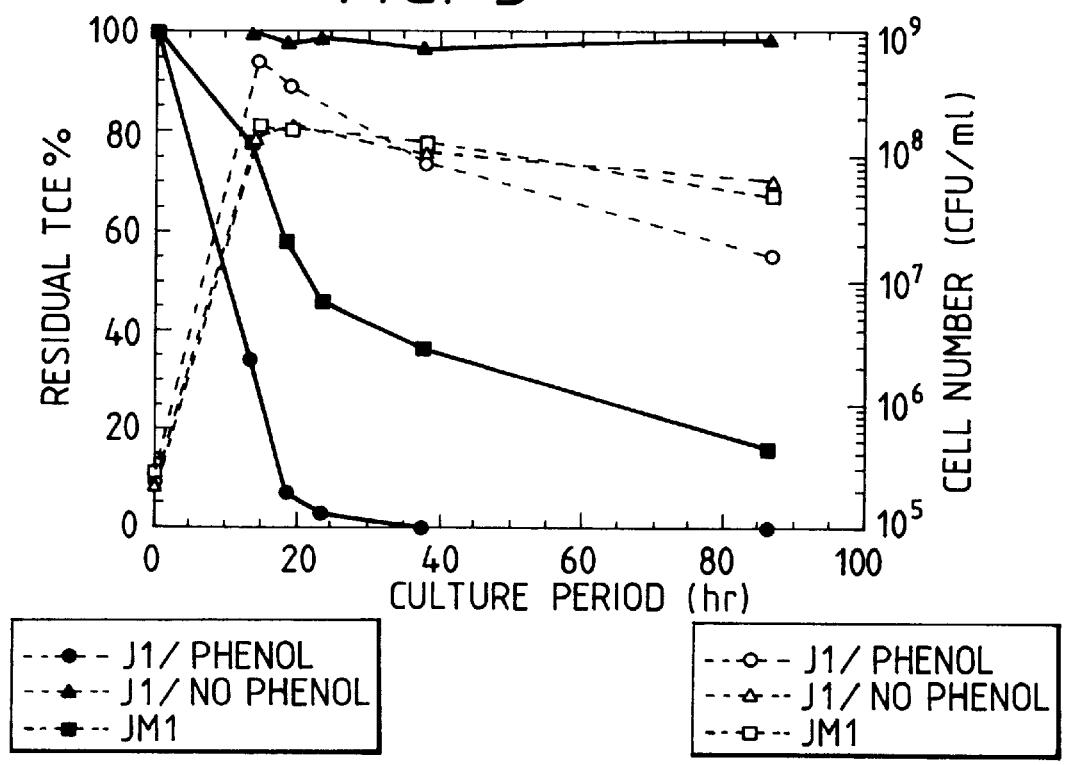
FIG. 5 is a graph showing TCE degradation and the growth of the bacterium in accordance with Example 11.

The results are depicted in FIG. 5.

| Group 1 | |
|---|---|
| Microorganism: | strain J1 |
| Carbon source in the culture medium: | 0.1% yeast extract |
| Inducer in the culture medium: | phenol (200 ppm) |
| Group 2 | |
| Microorganism: | strain J1 |
| Carbon source in the culture medium: | 0.1% yeast extract |
| Inducer in the culture medium: | none |
| Group 3 | |
| Microorganism: | strain JM1 |
| Carbon source in the culture medium: | 0.1% yeast extract |
| Inducer in the culture medium: | none |

Remediation of Contaminated Soil Using Strain JM1

(Examples 12–16)

EXAMPLE 12

Degradation of TCE in Soil Using Strain JM1 (15° C., Brown Forest Soil)

Test samples were prepared in the same manner as in Example 8 except that the content of the vials was changed to a mixture of the following (a)–(d), and stationary culture was done at 15° C., which is close to the actual soil temperature. Change of the TCE concentration with time was determined by head space gas chromatography.

As a control, a sample was prepared TCE concentration was determined in the same manner as above except that strain JM1 was not added.

Figure 6:
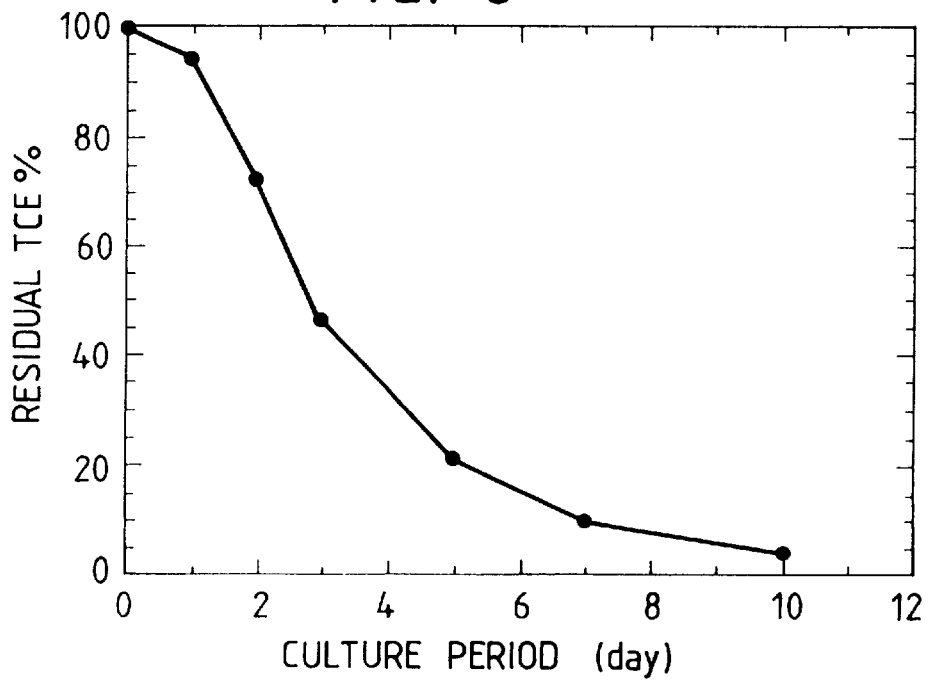
FIG. 6 is a graph showing TCE degradation in accordance with Example 12.

Change of TCE concentration with time was determined as a residual percentage of TCE to the control. The results are depicted in FIG. 6.

(a) contaminant: TCE (20 ppm)

(b) 1 ml of M9 medium containing 0.1% of yeast extract (c) 4 g of brown forest soil (d) 0.1 ml of JM1 culture

EXAMPLE 13

Degradation of TCE in Soil Using Strain JM1 (15° C., Loam Soil)

Figure 7:
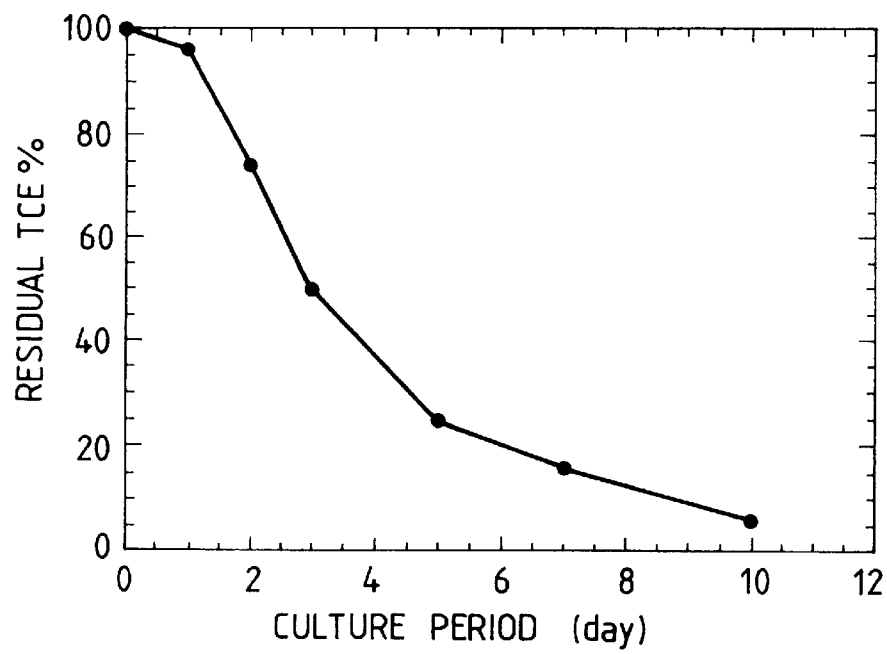
FIG. 7 is a graph showing TCE degradation in accordance with Example 13.

Decrease of the TCE quantity with time was measured in the same manner as in Example 12 except that the sample soil was changed to loam soil, and the residual percentage of TCE to the control was calculated. The results are depicted in FIG. 7.

EXAMPLE 14

Degradation of TCE in Soil Using Strain JM1 (15° C., Fine Sand Soil)

Figure 8:
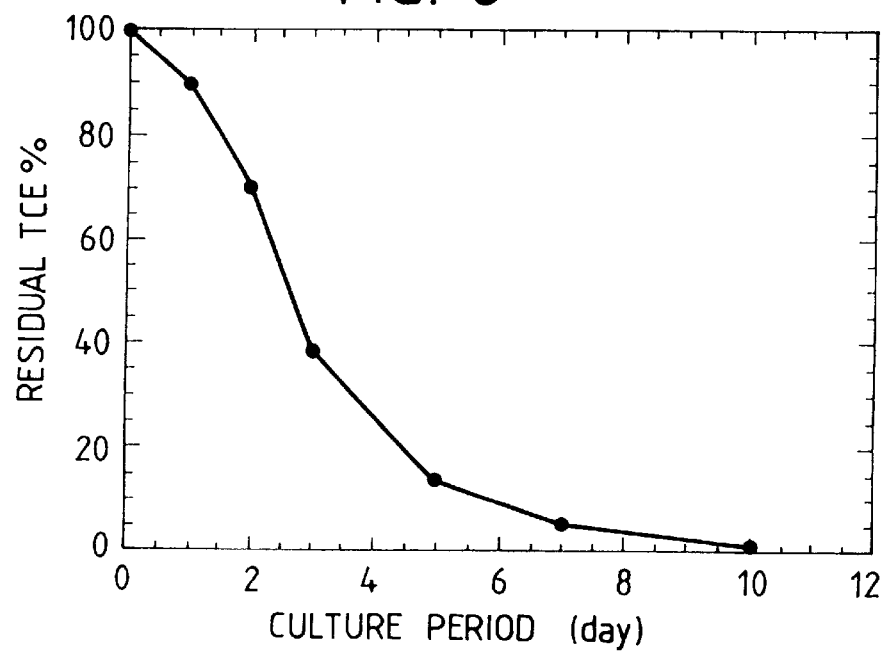
FIG. 8 is a graph showing TCE degradation in accordance with Example 14.

Decrease of TCE concentration with time was measured in the same manner as in Example 12 except that the sample soil was changed to fine sand soil (silt content about 10%), and the residual percentage of TCE to the control was calculated. The results are depicted in FIG. 8.

EXAMPLE 15

Degradation of DCE in Soil Using Strain JM1 (15° C., Brown Forest Soil)

Figure 9:
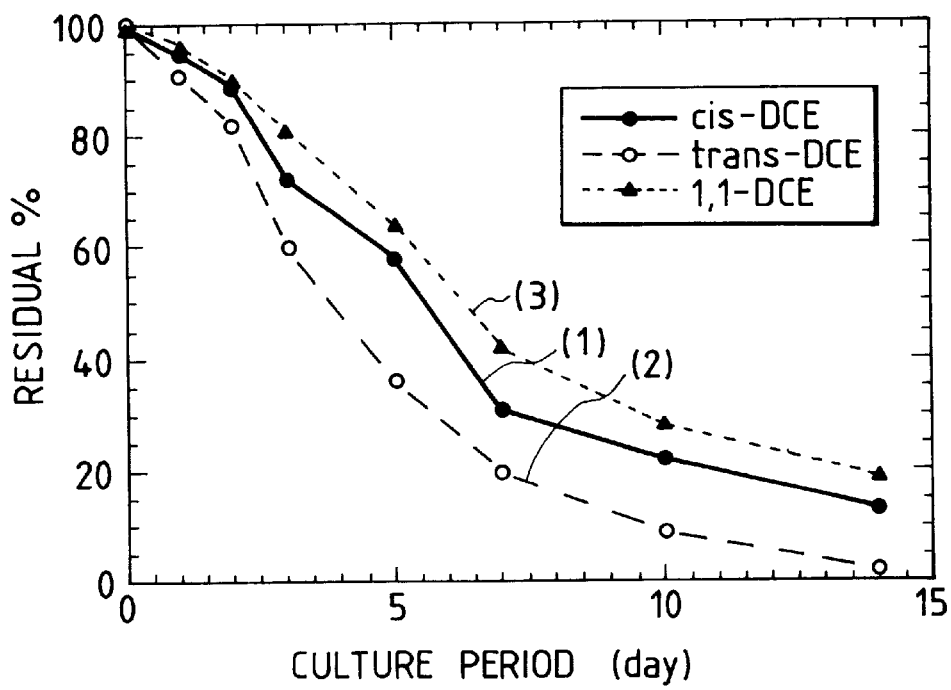
FIG. 9 is a graph showing DCE degradation in accordance with Example 15.

Decrease of DCE concentration with time was measured in the same manner as in Example 12 except that contaminant was changed to the each following type of DCE, and the residual percentage of DCE to the control was calculated. The results are depicted in FIG. 9.

(1) cis-1,2-dichloroethylene (5 ppm)
(2) trans-1,2-dichloroethylene (5 ppm)
(3) 1,1-dichloroethylene (5 ppm)

EXAMPLE 16

Degradation of Phenol in Soil Using Strain JM1 (15° C. Brown Forest Soil)

Decrease of phenol concentration with time was measured in the same manner as in Example 12 except that contaminant was changed to phenol.

Quantitative determination of phenol was made in accordance with Japanese Industrial Standards (JIS K0102-1993, 28.1) using aminoantipyrine.

Figure 10:
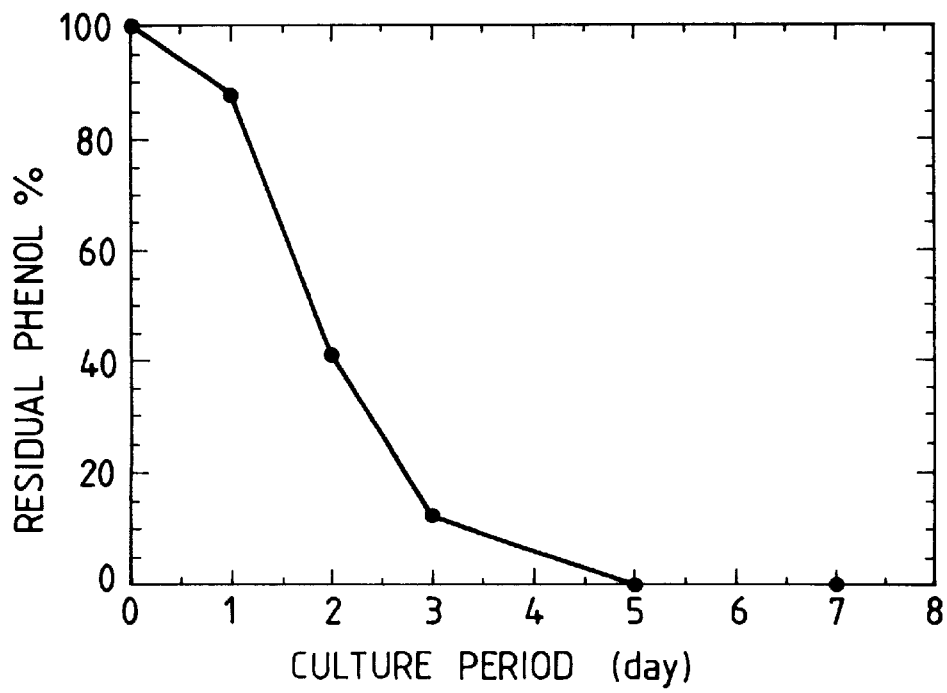
FIG. 10 is a graph showing the degradation of phenol in accordance with Example 16.

The residual percentage of phenol to the control was calculated. The results are depicted in FIG. 10.

Remediation of Contaminated Gas Using Strain JM1

(Examples 17–22)

EXAMPLE 17

Degradation of TCE in a Gas Phase by Aeration of Culture of Strain JM1

A liquid culture of strain JM1 was prepared in the same manner as in Example 8.

Next a plurality of vials each containing 30 ml of M9 medium supplemented with 0.1% of yeast extract and 0.1 ml of the above culture of strain JM1 were prepared. Then air passing through a saturated aqueous solution of TCE was introduced into the culture in the vials at a flow rate of 60 ml/min for 30 minutes. Then shaking culture was done at 30° C. after the vials were sealed with a butyl rubber stopper and an aluminum seal.

The concentration of TCE was determined by head space gas chromatography, and decrease of TCE with time was determined.

As a control, TCE concentration was determined for a sample prepared in the same manner as above except that strain JM1 was not added.

Figure 11:
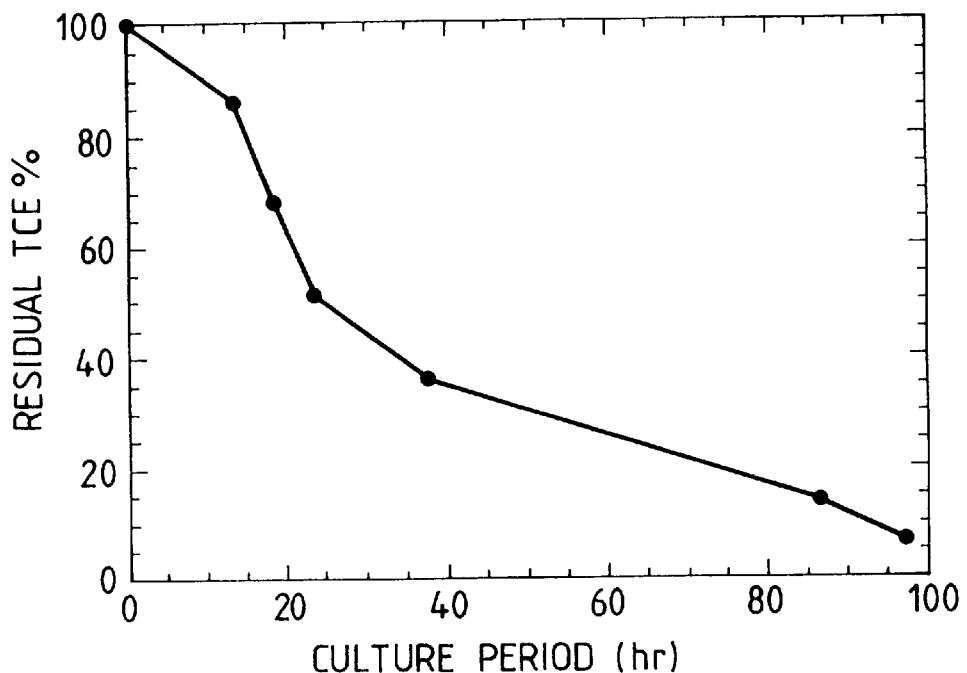
FIG. 11 is a graph showing TCE degradation in accordance with Example 17.

The change of the TCE concentration with time was calculated as the residual percentage of TCE to the control. The results are depicted in FIG. 11.

EXAMPLE 18

Degradation of DCE in a Gas Phase by Aeration of Culture of Strain JM1

Decrease of the DCE concentration with time was determined in the same manner as in Example 17 except that the air introduced into the vials was changed to the air passing through a saturated aqueous solution of DCE of any one of the following (1), (2) or (3).

Figure 12:
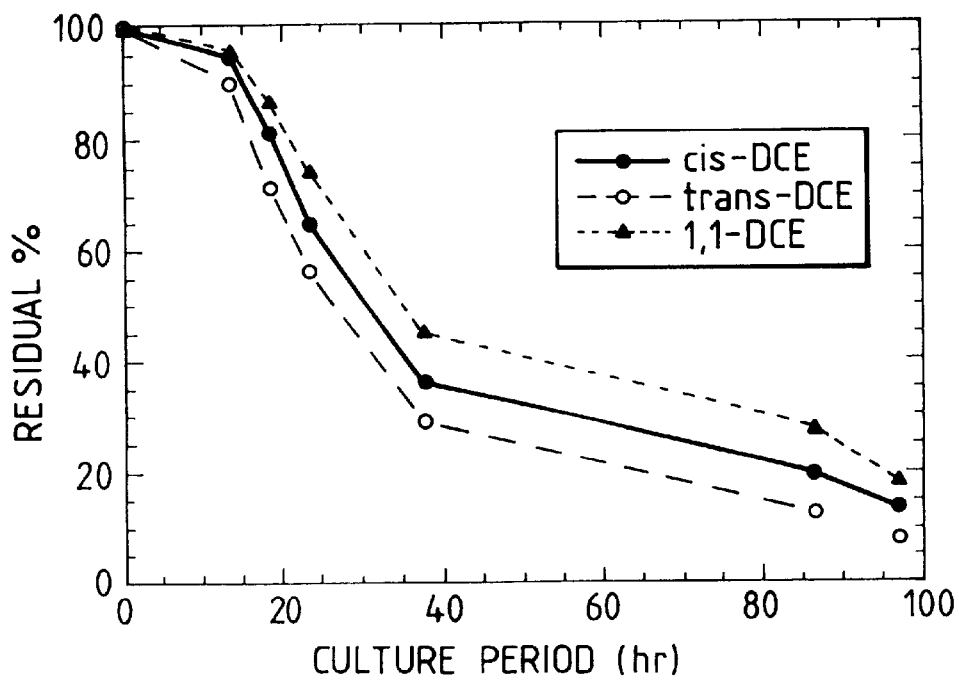
FIG. 12 is a graph showing DCE degradation in accordance with Example 18.

And the residual percentage of DCE to the control DCE concentration was calculated. The results are depicted in FIG. 12.

(1) cis-1,2-dichloroethylene
(2) trans-1,2-dichloroethylene
(3) 1,1-dichloroethylene

EXAMPLE 19

Degradation of Toluene in a Gas Phase by Aeration of Culture of Strain JM1

Decrease of the toluene concentration with time was determined in the same manner as in Example 17 except that air introduced into the vials was changed to the air used for aerating a saturated aqueous solution of toluene. The concentration of toluene in a gas phase was determined by head space gas chromatography.

Figure 13:
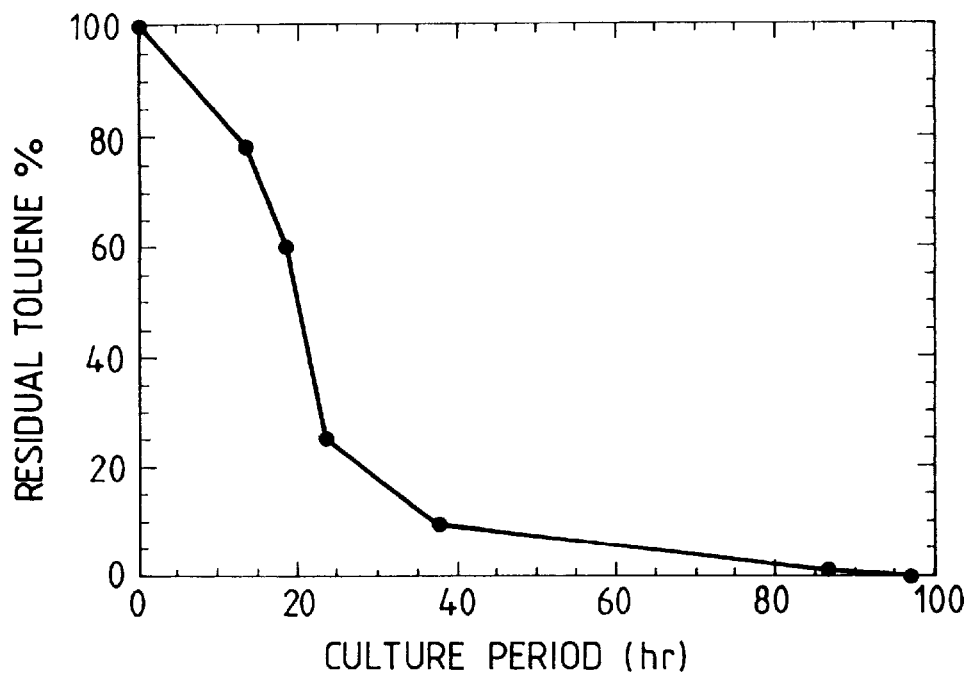
FIG. 13 is a graph showing the degradation of toluene in accordance with Example 19.

The residual percentage of toluene to the control toluene concentration was calculated as in Example 17. The results are depicted in FIG. 13.

EXAMPLE 20

Degradation of TCE in a Gas Phase by Aeration of Soil Containing Strain JM1

A culture of strain JM1 was prepared in the same manner as in Example 8.

Next prepared are a plurality of vials each containing 30 ml of M9 medium supplemented with 0.1% of yeast extract and 0.1 ml of the above culture of strain JM1.

Then sterilized brown forest soil was added to each vial to reach the surface of the culture medium, and the vials were sealed with a butyl rubber stopper. After vials were left standing overnight, the butyl rubber stopper was removed and the superfluous medium was discarded by decantation.

Then air passing through a saturated TCE aqueous solution was introduced into the soil in the vials at a flow rate of 60 ml/min for 30 minutes followed by stationary culture at 30° C. after each vial was sealed with a butyl rubber stopper and an aluminum seal.

Figure 14:
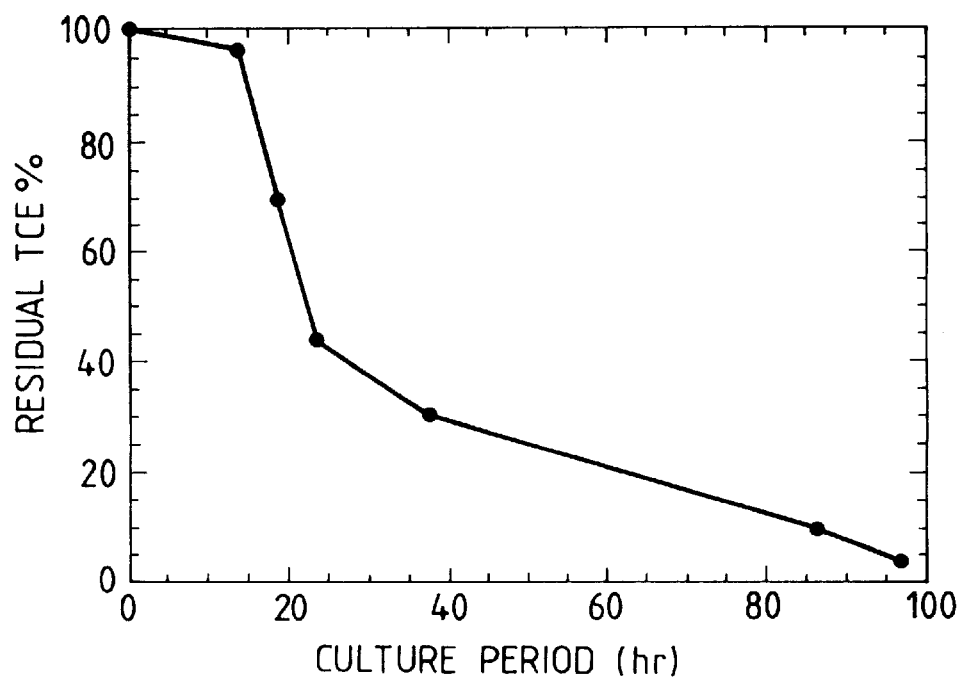
FIG. 14 is a graph showing TCE degradation in accordance with Example 20.

The residual percentage of TCE to the control TCE was calculated as in Example 17. The results are depicted in FIG. 14.

EXAMPLE 21

Degradation of TCE in a Gas Phase by Continuous Aeration of Liquid Culture of Strain JM1

Figure 15:
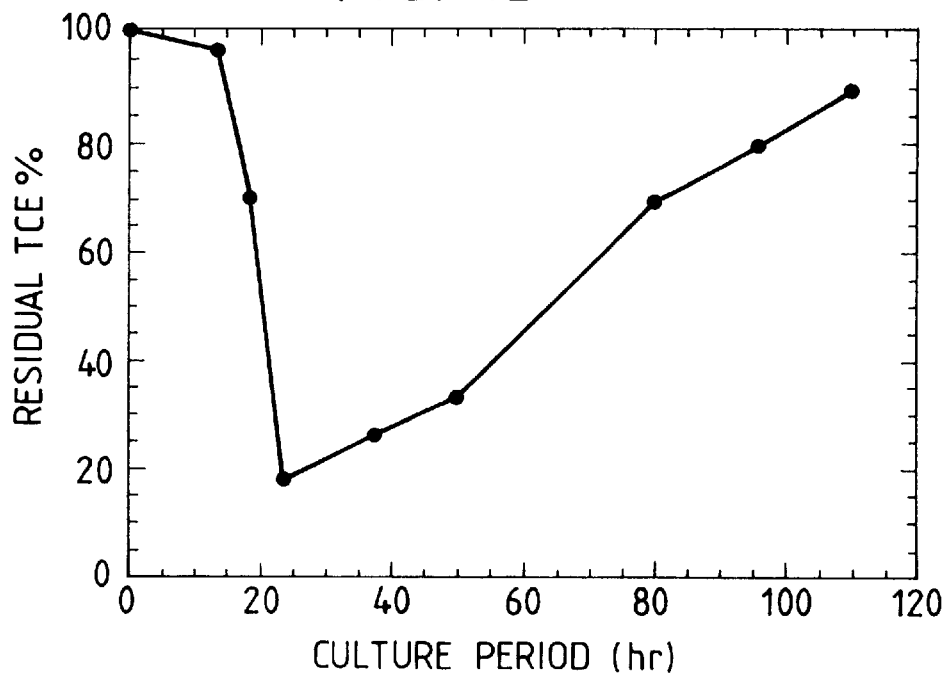
FIG. 15 is a graph showing TCE degradation in accordance with Example 21.

A plurality of vials were prepared, and 0.1 ml of the same culture of strain JM1 as used in Example 17 and 30 ml of M9 medium supplemented with 0.1% of yeast extract were put into each vial. Then, while air passing through a saturated aqueous solution of TCE was continuously introduced into the culture in vials at a flow rate of 0.5 ml/min, stationary culture was carried out at 30° C. The concentration of TCE was determined with time by quantitatively determining the TCE concentration in the air exhausted from the vial by gas chromatography. The residual percentage of TCE to the control was calculated in the same manner as in Example 17. The results are depicted in FIG. 15.

EXAMPLE 22

Degradation of TCE in a Gas Phase by Continuous Aeration of Soil Containing Strain JM1

Figure 16:
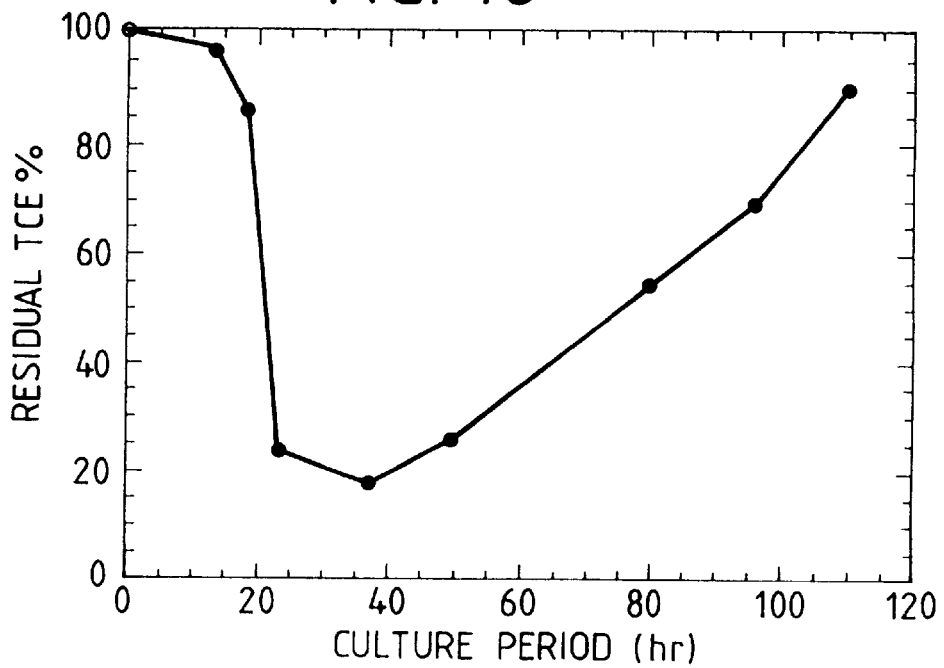
FIG. 16 is a graph showing TCE degradation in accordance with Example 22.

A plurality of vials were prepared, and 0.1 ml of the same culture medium of strain JM1 as in Example 17 and 30 ml of M9 medium supplemented with 0.1% yeast extract were put into each vial and in addition sterilized brown forest soil was added to each vial to reach the surface of the culture medium. Each vial was sealed with a butyl rubber stopper and left standing overnight at 30° C., and then the excess culture medium was discarded by decantation. Then while air passing through a saturated aqueous solution of TCE was continuously introduced into the soil in vials at a flow rate of 0.5 ml/min, stationary culture was carried out at 30° C. The quantity of TCE was determined with time by determining TCE concentration in the air exhausted from the vial by gas chromatography. The residual percentage of TCE to the control was calculated in the same manner as in Example 17. The results are depicted in FIG. 16.

What is claimed is:

1. A biologically pure bacterium strain JM1 (FERM BP-5352).

2. A process for degrading organic compounds comprising the steps of:

bringing a microorganism according to claim 1 into contact with the organic compounds under conditions such that the microorganism can exhibit a degradation activity for the organic compounds; and degrading the organic compounds with the microorganism.

3. A process for remedying an environment polluted with an organic compound comprising the steps of:

bringing a microorganism according to claim 1 into contact with the environment under conditions such that the microorganism can exhibit a degradation activity for the organic compounds; and degrading the organic compounds with the microorganism to remedy the environment.

4. The process according to claim 2 or 3, wherein the organic compounds are aromatic compounds.

5. The process according to claim 4, wherein the aromatic compounds are at least one of phenol, toluene or cresol.

6. The process according to claim 2 or 3, wherein the organic compounds are chlorinated aliphatic hydrocarbon compounds.

7. The process according to claim 6, wherein the chlorine compounds are at least one of trichloroethylene or dichloroethylene.

8. The process according to claim 2, wherein the microorganism is held by a carrier and the carrier is brought into contact with the organic compounds.

9. The process for remedying an environment according to claim 3, wherein the environment is an aqueous medium.

10. The process for remedying an environment according to claim 3, wherein a liquid containing the microorganism is introduced into the soil.

11. The process for remedying an environment according to claim 10, wherein the soil is introduced into a liquid containing the microorganism.

12. The process for remedying an environment accoring the claim 3, wherein a liquid containing the microorganism is introduced into the soil.

13. The process for remedying an environment according to claim 12, wherein the liquid containing the microorganism is introduced into the soil and at the same time a substance stimulating the growth of the microorganism is introduced into the soil to allow the microorganism to grow in the soil.

14. The process for remedying an environment according to claim 13, wherein the substance is a nutrient for the microorganism.

15. The process for remedying an environment according to claim 13, therein the substance is oxygen.

16. The process for remedying an environment according to claim 12, wherein introduction of the liquid into the soil is carried out by applying pressure via a well provided into the soil.

17. The process for remedying an environment according to claim 3, wherein the environment is a gas.

18. The process for remedying an environment according to claim 17, wherein the gas is introduced into a liquid phase containing the microorganism.

19. A process for detecting a presence or absence of strain JM1 (FERM BP-5352) expressing oxygenase from a sample containing strain J1 (FERM BP-5102) which expresses oxygenase when induced, comprising the steps of:

(a) selecting a culture medium for culturing the sample so that colonies of strains J1 and JM1 are grown, the colony of strain JM1 showing substantially no time lag between the growth of the colony and the expression of detectable characteristics showing the presence of the oxygenase, and the colony of strain J1 showing a time lag between the growth of the colony and the expression of detectable characteristics showing the presence of oxygenase when a sample is cultured in the presence of precursor which is oxidized by oxygenase, the oxidized precursor exhibiting color development or fluorescence emission not exhibited by the precursor and which induces oxygenase in strain J1;

(b) culturing the sample in the culture medium containing the precursor; and (c) detecting the presence or absence of a colony having substantially no time lag between the growth of the colony and the expression of detectable characteristics showing the presence of oxygenase as a colony of strain JM1.

20. The process for detecting a microorganism according to claim 19, wherein the precursor is indole.

21. The process for detecting a microorganism according to claim 19, wherein the precursor is creosote.

22. The process for detecting a microorganism according to claim 19, wherein the precursor is o-aminophenol.

23. The process for detecting a microorganism according to claim 19, wherein the precursor is a substance having a catechol skeleton.

24. The process for detecting a microorganism according to claim 23, wherein the substance is at least one selected from the group consisting of catechol, 3-methylcatechol and 3-trifluoromethylcatechol.

25. The process for detecting a microorganism according to claim 19, wherein the precursor is phenol.

26. The process for detecting a microorganism according to claim 19, wherein the precursor is 3-trifluoromethylphenol.

27. The process for detecting a microorganism according to claim 19, wherein the precursor is cresol.

28. The process for detecting a microorganism according to claim 19, wherein oxidation of the precursor by oxygenase forms a fluorescent oxide.

29. The process for detecting a microorganism according to claim 28, wherein the precursor is indole.

30. The process for detecting a microorganism according to claim 29, wherein fluorescence of indoxyl is detected.

31. The process according to claim 28, wherein the fluorescence emitted is measured.

32. The process for detecting a microorganism according to claim 31, wherein the fluorescence is detected using a flow cytometer.

33. The process for detecting a microorganism according to claim 31, wherein the fluorescence is detected using a fluorescence microscope.

34. A process for obtaining strain JM1 (FERM BP-5352) expressing oxygenase from a sample containing (i) strain JM1 and (ii) strain J1 (FERM BP-5102) expressing oxygenase when induced, comprising the steps of:

(a) culturing the sample in a culture medium containing a nutrient and a precursor (i) which is oxidized by an oxygenase, the oxidized precursor exhibiting color development or fluorescence emission which is not exhibited by the precursor, and (ii) which induces strain J1 to express oxygenase, to grow strain J1 and strain JM1 in the sample and form colonies thereof; and (b) detecting and separating a colony showing substantially no time lag between a growth of the colony and the expression of characteristics which show the presence of oxygenase, the characteristics originating from the oxidized precursor.

35. A kit for selectively detecting strain JM1 (FERM BP-5352) expressing oxyqenase from a sample containing strain J1 (FERM BP-5102 which expresses oxygenase when induced, comprising:

(a) a culture medium for culturing the sample so that colonies of strain J1 and strain JM1 are grown, the colony of strain JM1 showing substantially no time lag between the growth of the colony and the expression of characteristics showing the presence of oxygenase when the sample is cultured in the presence of a precursor (i) which is oxidized by oxygenase, the oxidized precursor exhibiting color development or fluorescence emission not exhibited by the precursor and (ii) which induces oxygenase in strain J1; and (b) a precursor which is oxidized by oxygenase to an oxidized precursor which exhibits color development or fluorescence emission not exhibited by the precursor.

* * * * *

UNITED STATES PATENT AND TRADEMARK OFFICE
CERTIFICATE OF CORRECTION

PATENT NO.   : 6,004,772
DATED        : December 21, 1999
INVENTOR(S)  : Takeshi Imamura et al.

Page 1 of 3

It is certified that error appears in the above-identified patent and that said Letters Patent is hereby corrected as shown below:

ON THE TITLE E [56] References Cited:

U.S. PATENT DOCUMENTS, "Georgrou et al." should read --Georgiou et al.--;
OTHER PUBLICATIONS (Page 1), after "Little et al.": "rium," should read --rium",--; and
OTHER PUBLICATIONS (Page 2), "Vandenbugh et al., "Metabolsim of Volatile. . . Pseudomonas fluorescens", Appl. & Envir. Micro,m vol. 54, No. 10, Oct. 1988, pp. 2578-2579." should be deleted.

ON THE TITLE PAGE [57] ABSTRACT:
Line 6, "stimulates" should read --stimulate--.

Column 1:
Line 42, "develop." should read --be developed.--.

Column 4:
Line 34, "a" should be deleted.

Column 7:
Line 32, "naturally" should be --is naturally--.

Column 8:
Line 16, "above mentioned" should read --above-mentioned--;
Line 37, "above mentioned" should read --above-mentioned--;
Line 39, "by" should read --By--;
Line 55, "have" should read --has--; and
Line 64, "careful" should read --carefully--.

Column 11:
Line 4, "microorganisms" should read --microorganism--.

Column 12:
Line 37, "is" should read --are--.

UNITED STATES PATENT AND TRADEMARK OFFICE
CERTIFICATE OF CORRECTION

PATENT NO. : 6,004,772
DATED : December 21, 1999
INVENTOR(S) : Takeshi Imamura et al.

It is certified that error appears in the above-identified patent and that said Letters Patent is hereby corrected as shown below:

Column 13:
Line 23, "promote" should read --promotes--;
Line 66, "is" should read --are--; and
Line 67, "case" should read --cases--.

Column 14:
Line 1, "exhibit." should read --exhibited.--;
Line 2, "is" should read --are--;
Line 24, "degrading"hould read --degrade--; and
Line 27, "remedying" should read --remedy--.

Column 15:
Line 19, "C120 C230" should read --C120  C230--.

Column 16:
Line 27, "o" should read --of--;
Line 36, "colonies," should read --colony,--;
Line 54, "extract, respectively" should read --extract, respectively,--; and
Line 56, "was" should be deleted.

Column 17:
Line 17, "an" should read --a--;
Line 37, "an" should read --a--;
Line 43, "an" should read --a--; and
Line 67, "an" should read --a--.

Column 18:
Line 5, "an" should read --a--.

Column 19:
Line 29, "stoppers" should read --stopper--.

UNITED STATES PATENT AND TRADEMARK OFFICE
CERTIFICATE OF CORRECTION

PATENT NO. : 6,004,772
DATED : December 21, 1999
INVENTOR(S) : Takeshi Imamura et al.

It is certified that error appears in the above-identified patent and that said Letters Patent is hereby corrected as shown below:

Column 20:
Line 22, "O.1%" should read --0.1%--; and
Line 41, "was" should be deleted.

Column 23:
Line 19, "an organic compound" should read --organic compounds--;
Line 43, "a liquid containing the microorganism is" should read --the environment is soil--;
Line 44, should be deleted;
Line 48, "accoring" should read --according--; and
Line 61, "therein" should read --wherein--.

Column 24:
Line 53, "process" should read --process for detecting a microorganism--.

Column 25:
Line 12, "oxygenase" should read --oxygenase--; and
Line 13, "(FERM BP-5102" should read (FERM BP-5102)--.

Signed and Sealed this

Nineteenth Day of June, 2001

*Attest:*

*Attesting Officer*

NICHOLAS P. GODICI
*Acting Director of the United States Patent and Trademark Office*